(12) United States Patent
Rourke et al.

(10) Patent No.: US 10,127,502 B2
(45) Date of Patent: Nov. 13, 2018

(54) SYSTEM AND METHOD FOR WEB-BASED CLAIM MANAGEMENT

(75) Inventors: Timothy Rourke, San Diego, CA (US); Sherry Pound, San Diego, CA (US); Emebet Solomon Selassie, San Diego, CA (US); Rene Agamata Tangonan, San Diego, CA (US)

(73) Assignee: MEDIMPACT HEALTHCARE SYSTEMS, INC., San Diego, CA (US)

( * ) Notice: Subject to any disclaimer, the term of this patent is extended or adjusted under 35 U.S.C. 154(b) by 0 days.

(21) Appl. No.: 12/845,674

(22) Filed: Jul. 28, 2010

(65) Prior Publication Data

US 2011/0029321 A1 Feb. 3, 2011

Related U.S. Application Data

(60) Provisional application No. 61/271,964, filed on Jul. 28, 2009.

(51) Int. Cl.
*G06Q 50/00* (2012.01)
*G06Q 10/00* (2012.01)
(Continued)

(52) U.S. Cl.
CPC ....... *G06Q 10/00* (2013.01); *G06F 17/30896* (2013.01); *G06F 19/328* (2013.01); *G06Q 20/102* (2013.01); *G06Q 50/22* (2013.01)

(58) Field of Classification Search
CPC .. G06F 19/328; G06F 50/22; G06F 17/30896; G06F 10/00; G06Q 50/22; G06Q 20/102
(Continued)

(56) References Cited

U.S. PATENT DOCUMENTS

| 5,301,105 A | 4/1994 | Cummings, Jr. |
| 5,704,044 A | 12/1997 | Tarter et al. |

(Continued)

FOREIGN PATENT DOCUMENTS

| WO | WO 95/24010 | 9/1995 |
| WO | WO 97/44752 | 11/1997 |

OTHER PUBLICATIONS

Infocrossing Healthcare Services, Inc., Prescription Drug Event (PDE) Submission Process Summary, 2007, Infocrossing, pp. 1-2.*

(Continued)

*Primary Examiner* — Joy Chng
(74) *Attorney, Agent, or Firm* — Mintz, Levin, Cohn, Ferris, Glovsky and Popeo, P.C.

(57) ABSTRACT

The system includes a variety of aspects which allow users to efficiently receive reimbursement for claims. Claims accepted by CMS result in reimbursement for claimants. Claims rejected by CMS represent lost revenue for claimants. In order to maximize accepted claims and minimize rejected claims, the system provides for the generation of more accurate PDE files for submission and for the accumulation and formatting of information received from CMS to facilitate correction of PDE errors. These aspects work in tandem to minimize lost revenue for the claimant. Further, aspects described herein help minimize PDE error rates. Such minimization of errors can affect the reputation, business model, credibility, and competitive posture of Part D plan sponsors. Accordingly, minimization of PDE error rates is important to the overall design, function, and profitability of any Medicare Part D plan sponsor.

12 Claims, 35 Drawing Sheets

(51) Int. Cl.
*G06F 15/16* (2006.01)
*G06F 17/30* (2006.01)
*G06F 3/01* (2006.01)
*G06Q 20/10* (2012.01)
*G06F 19/00* (2018.01)
*G06Q 50/22* (2018.01)

(58) Field of Classification Search
USPC .................................. 705/2–3; 707/740, 769
See application file for complete search history.

(56) References Cited

U.S. PATENT DOCUMENTS

| | | | |
|---|---|---|---|
| 5,737,539 | A | 4/1998 | Edelson et al. |
| 5,845,255 | A | 12/1998 | Mayaud |
| 6,108,635 | A | 8/2000 | Herren et al. |
| 6,195,612 | B1 | 2/2001 | Pack-Harris |
| 6,283,761 | B1 | 9/2001 | Joao |
| 7,165,077 | B2 | 1/2007 | Kalies |
| 7,490,047 | B2 | 2/2009 | Brown et al. |
| 7,505,917 | B2 | 3/2009 | Howe et al. |
| 7,949,580 | B1 | 5/2011 | Boyer et al. |
| 8,060,379 | B1 | 11/2011 | Pinsonneault et al. |
| 8,069,059 | B2 | 11/2011 | Howe et al. |
| 8,099,295 | B2 | 1/2012 | Virdee et al. |
| 8,265,950 | B2 | 9/2012 | Howe et al. |
| 8,346,571 | B2 | 1/2013 | Kalies, Jr. |
| 2001/0037216 | A1 | 11/2001 | Oscar et al. |
| 2002/0002495 | A1 | 1/2002 | Ullman |
| 2002/0049617 | A1 | 4/2002 | Lencki et al. |
| 2002/0082863 | A1 | 6/2002 | Kleinke |
| 2002/0095316 | A1 | 7/2002 | Toan et al. |
| 2002/0111832 | A1 | 8/2002 | Judge |
| 2002/0120473 | A1* | 8/2002 | Wiggins ............... G06Q 10/087 705/4 |
| 2002/0147617 | A1 | 10/2002 | Schoenbaum et al. |
| 2002/0169727 | A1 | 11/2002 | Melnick et al. |
| 2002/0183965 | A1 | 12/2002 | Gogolak |
| 2003/0154106 | A1 | 8/2003 | Marks |
| 2004/0054685 | A1* | 3/2004 | Rahn ................... G06Q 40/02 |
| 2004/0073457 | A1 | 4/2004 | Kalies |
| 2004/0133452 | A1* | 7/2004 | Denny, Jr. ............ G06F 19/328 705/2 |
| 2004/0143171 | A1 | 7/2004 | Kalies |
| 2004/0143594 | A1 | 7/2004 | Kalies |
| 2004/0148195 | A1 | 7/2004 | Kalies |
| 2004/0148196 | A1 | 7/2004 | Kalies |
| 2004/0148198 | A1 | 7/2004 | Kalies |
| 2004/0230502 | A1 | 11/2004 | Fiacco et al. |
| 2005/0060188 | A1 | 3/2005 | Valley |
| 2005/0065821 | A1 | 3/2005 | Kalies, Jr. |
| 2005/0071193 | A1 | 3/2005 | Kalies |
| 2005/0071200 | A1 | 3/2005 | Franklin et al. |
| 2005/0240442 | A1 | 10/2005 | Lapsker |
| 2005/0251429 | A1* | 11/2005 | Ammer .................. G06Q 10/10 705/4 |
| 2005/0261939 | A1 | 11/2005 | Augspurger et al. |
| 2005/0283259 | A1 | 12/2005 | Wolpow |
| 2006/0020514 | A1 | 1/2006 | Yered |
| 2006/0116905 | A1 | 6/2006 | Yered |
| 2006/0129357 | A1 | 6/2006 | Francis et al. |
| 2006/0178915 | A1 | 8/2006 | Chao |
| 2006/0184391 | A1 | 8/2006 | Barre et al. |
| 2006/0271402 | A1 | 11/2006 | Rowe et al. |
| 2007/0011025 | A1* | 1/2007 | Cracchiolo ............ G06Q 20/10 705/2 |
| 2007/0050210 | A1 | 3/2007 | Wiley, II |
| 2007/0106623 | A1 | 5/2007 | Melnick et al. |
| 2007/0250341 | A1 | 10/2007 | Howe et al. |
| 2008/0312956 | A1 | 12/2008 | Momita et al. |
| 2009/0076868 | A1 | 3/2009 | Malone et al. |
| 2009/0144082 | A1 | 6/2009 | Selbst et al. |
| 2009/0177488 | A1 | 7/2009 | Unland et al. |
| 2009/0177490 | A1 | 7/2009 | Howe et al. |
| 2009/0281823 | A1 | 11/2009 | Hardaway |
| 2009/0281824 | A1 | 11/2009 | Hardaway |
| 2009/0319311 | A1* | 12/2009 | Mi ........................ G06Q 10/10 705/2 |
| 2009/0326975 | A1 | 12/2009 | Hardaway et al. |
| 2010/0057489 | A1 | 3/2010 | Howe et al. |
| 2010/0161351 | A1 | 6/2010 | Howe et al. |
| 2010/0217622 | A1 | 8/2010 | Brown et al. |
| 2010/0287002 | A1 | 11/2010 | Barre et al. |
| 2010/0312578 | A1 | 12/2010 | Hardaway |
| 2011/0054935 | A1 | 3/2011 | Hardaway |

OTHER PUBLICATIONS

Department of Health and Human Services, Requirements for Submitting Prescription Drug Event (PDE) Data, Apr. 27, 2006, Centers for Medicare and Medicaid Services, pp. 1-92.*

Centers for Medicare & Medicaid Services (CMS), 2006 Prescription Drug Event Data Training Participant Guide, Jul. 2006, pp. 1-222.*

Infocrossing Healthcare Services, Inc., Prescription Drug Event (PDE) Submission Process Summary, 2007, Infocrossing, pp. 1-2 (Year: 2007).*

Department of Health and Human Services, Requirements for Submitting Prescription Drug Event (PDE) Data, Apr. 27, 2006, Centers for Medicare and Medicaid Services, pp. 1-92 (Year: 2006).*

Centers for Medicare & Medicaid Services (CMS), 2006 Prescription Drug Event Data Training Participant Guide, Jul. 2006, pp. 1-222 (Year: 2006).*

"Cost Sharing Strategies for OHP Medical Services." pp. 1-5. Revised Jul. 5, 2001.

Laing, R.O., et al., "Tuberculosis Drug Issues: Prices, Fixed Dose Combination Products and Second Line Drugs", Journal Tuberculosis Disease, 4(12) S194-S207 (Feb. 2000).

Huskamp, H.A., et al., "The Medicare Prescription Drug Benefit: How Will the Game be Played?" Health Affairs, 19(2) 8-23 (Mar.-Apr. 2000).

Lipton, H.L., et al., "Managing the Pharmacy Benefit in Medicare HMOs: What Do We Really Know?" Health Affairs, 19(2) 42-58 (Mar.-Apr. 2000).

MedImpact Medicare Part D 2009 Pre-Processing Drug List (PPDL) White Paper, Updated Mar. 25, 2008. pp. 1-5.

MedImpact Medicare Part D 2008 Pre-Processing Drug List (PPDL) White Paper, Updated Mar. 25, 2008. pp. 1-5.

MedImpact Medicare Part D Pre-Processing Drug List (PPDL) White Paper, Updated Jul. 20, 2006. pp. 1-5.

MedImpact Medicare Part D Drug List White Paper, Oct. 13, 2005. pp. 1-4.

Comments of Generic Pharmaceutical Association for the Public Meeting on Proposed Changes to the National Drug Code System; RIN 0910-AA49; Nov. 24, 2006; 7 pages.

PCT International Search Report, dated Jul. 8, 2007, in PCT/US06/42976.

Medicare Program: Revisions to the Medicare Advantage and Prescription Drug Benefit Programs; The Federal Register (FIND73.096); May 16, 2008; Source: Dept. of Health and Human Services.

* cited by examiner

Medimpact®
*Delivering • Flexible • Choice*

| HOME | SEARCH | REPORTS | FAQ | | | | | | | | | | | | SIGN OUT |
|------|--------|---------|-----|---|---|---|---|---|---|---|---|---|---|---|----------|

PDE EDIT DASHBOARD

| PDE Edit Code | 30 | 31 | 32 | 33 | 34 | 35 | 36 | 37 | 38 | 39 | 40 | 41 | 42 | Grand Total |
|---|---|---|---|---|---|---|---|---|---|---|---|---|---|---|
| 603 | | | | | | | | | | | | | | 1 |
| 631 | | | | | | | | | | | | | | 11 |
| 694 | | | | | | | | | | | | | | 13 |
| 700 | | | | | | | | | | | | 4 | | 19 |
| 702 | | | | | | | | | | 3 | | | 11 | 14 |
| 704 | | | | | | | | | | 1 | 1 | | 8 | 8 |
| 705 | 130 | 127 | 130 | 111 | 122 | 36 | 3 | 32 | 20 | 77 | 49 | 146 | 121 | 1104 |
| 706 | 35 | 29 | 31 | 30 | 48 | 24 | 1 | 28 | 23 | 4 | 14 | 8 | 21 | 296 |
| 707 | 25 | 22 | 31 | 53 | 31 | 29 | 2 | 38 | 53 | 26 | 45 | 25 | 16 | 396 |
| 708 | | | | 9 | 7 | 4 | | | | 1 | | | 8 | 29 |
| 712 | | | | | 5 | 3 | | | | | | | | 4 |
| 714 | | | | | | | | | | | | | | 5 |
| 715 | 68 | 69 | 44 | 41 | 46 | 63 | 4 | 13 | 16 | 7 | 10 | 13 | 19 | 413 |
| 716 | | 11 | 30 | 9 | 12 | 21 | 15 | 61 | 51 | 124 | 148 | 182 | 468 | 1132 |
| 717 | | | | | | 3 | | 6 | 6 | 2 | 2 | 11 | 79 | 109 |
| 718 | | | 5 | | | | | 8 | 4 | | 2 | | 42 | 62 |
| 720 | 1 | | 1 | 5 | 1 | 17 | 4 | 33 | 9 | 3 | 28 | 150 | 116 | 362 |
| 721 | | | | | | | | | 1 | | | | 4 | 4 |
| 735 | | | | | | | | | | | | 1 | | 6 |
| 737 | 1 | | 1 | | | 1 | 1 | 1 | | | | | | 1 |
| 738 | 3 | 4 | 7 | 5 | 6 | 10 | 3 | 20 | 24 | 17 | 37 | 22 | 33 | 191 |
| 739 | 5 | 8 | 5 | 5 | 5 | 5 | 1 | 5 | 7 | 4 | 5 | 15 | 20 | 90 |
| 740 | | | | | | | | | | | 1 | | 2 | 3 |
| 741 | | 1 | | | | | | | 1 | | | | | 1 |
| 777 | | | | | | | | | | | | | | 2 |
| 781 | | | | | 1 | 1 | | 1 | 7 | 3 | 4 | | | 37 |
| 784 | | 6 | 4 | 9 | 2 | 2 | | | 6 | | | | | 8 |
| 785 | | | | | | | | | | | | | | |
| 999 | 19 | 15 | 22 | 16 | 17 | 17 | 1 | 18 | 15 | 22 | 26 | 27 | 34 | 249 |

FIG. 6

MedImpact®
*Delivering • Flexible • Choice*

HOME  SEARCH  REPORTS  FAQ                                              SIGN OUT

— 620

CMS Submitter Code: [ ]            HQ: [ ]

Cycle: [ ] To [ ]                  Plan Year (yyyy): [ ]
              — 712
CMS Contract: [ ]                  CMS Plan: [ ]
              — 713
Submission Status: [ ]             HIC#: [ ]

PDE Edit Code: [ ]                 Cardholder ID: [ ]
                                              — 715
Review Status: [ ]

— 711
    [ SEARCH ]   OR   [ VIEW ALL ]

— 710

SEARCH AREA IS COLLAPSIBLE ONCE SEARCH RESULTS DISPLAYED 722    720   723

EXPORT    BULK UPDATE

| Submission Status | Review Status | Claim Number | Fill Date | PDE Edit Code | Cardholder ID | CMS Contract ID | CMS Plan ID | Last Updated By (and date) | Original Cycle | Current Cycle | LICS Level on Fill Date | LICS Level on Member | Select All ☐ |
|---|---|---|---|---|---|---|---|---|---|---|---|---|---|
| [VIEW] |  |  |  |  |  |  |  |  |  |  |  |  | ☐ |
| [VIEW] |  |  |  |  |  |  |  |  |  |  |  |  | ☐ |
| [VIEW] |  |  |  |  |  |  |  |  |  |  |  |  | ☐ |
| [VIEW] |  |  |  |  |  |  |  |  |  |  |  |  | ☐ |
| [VIEW] |  |  |  |  |  |  |  |  |  |  |  |  | ☐ |
| [VIEW] |  |  |  |  |  |  |  |  |  |  |  |  | ☐ |

Medimpact®
*Delivering • Flexible • Choice*

HOME   SEARCH   REPORTS   FAQ                                    SIGN OUT

— 620

Submission Status: [  ]          Plan Year: [  ]
CMS Contract:     [  ]          CMS Plan:  [  ]
Original Cycle:   [  ]          Current Cycle: [  ]
Claim ID:         [  ]          Cardholder ID: [  ]
Rx Number:        [  ]          Pharmacy ID:   [  ]
HIC #:            [  ]          Member LICS Level: [  ]
Fill Date:        [  ]          LICS Level on Claim: [  ]
Group:            [  ]          Division: [  ]
Region Code 1:    [  ]          Region Code 2: [  ]
PDE Edit Code:    [  ]          Adjustment Deletion Code: [  ]
Covered Plan Paid [  ]          Non Covered Plan Paid
  Amount:                         Amount: [  ]

Immediately Actionable PDE Edit: ☐
Need Eligibility Update: ☐

— 810

COMMENT

Review Status          Review Comment        Entered By          Entered Date
▸ New                  <text entered by user>  Auto-populate      Auto-populate    [SUBMIT]
  Referred to Plan
  Referred to Integreguard
  Referred to Medimpact
  Pending Retro-LICS
  Pending True-UP
  Pending CMS Update
  Not Reviewed
  Excluded
  Reserved

<HISTORY OF COMMENTS DISPLAY BELOW THIS WITH LATEST COMMENT AT TOP>

MedImpact®
*Delivering • Flexible • Choice*

HOME  SEARCH  REPORTS  FAQ                                                      SIGN OUT

+ PDE Summary Report

| EDIT REASON | New PDE Edits Current Cycle | PDE Edits For Current Month | Outstanding PDE edits Year to date |
|---|---|---|---|
| Enrollment/eligibility corrections needed (Edits 603, 700-707) | 178 | 1,838 | 1,838 |
| LICS related corrections needed (Edits 715-721) | 728 | 2,082 | 2,082 |
| NDC related corrections (Edits 735-741) | 35 | 202 | 202 |
| Pharmacy Service Provider ID issues (Edits 781-783) | - | 2 | 2 |
| Duplicate Edit reasons to be resolved (Edits 660, 777, 785 and 784) | - | 46 | 46 |
| CMS internal issues (999) | 34 | 249 | 249 |
| Others (775, 631, 694) |  | 24 | 24 |
| Total number of PDE edits | 975 | 4,443 | 4,443 |
| Percent of PDE records that have not been accepted on current file | 0.58% | 2.64% | 0.25% |

EXPORT

FIG. 11

PDE Tool: PDE Edits Dashboard

SELECT PLAN YEAR
To change the Plan Year and Submitter Code for PDE Edits, use the pulldown below.

Plan Year: 2009 ▼ [SUBMIT]

PDE EDITS SEARCH
To proceed to PDE Edits Search, click the link below.
☐ PDE Edits Search ← 1420

PDE EDITS - 2009 | 44
To view reports, click the corresponding (linked) total for a desired Edits Category and Status (New, Resubmitted, or Total YTD).
To export the results to a CSV File, click the "EXPORT RESULTS" button below.

| Edits Category | New (Current Cycle) | Resubmitted (Current Cycle) | Total YTD (Current Cycle) |
|---|---|---|---|
| Enrollment/Eligibility Edits | 274 | 256 | 530 |
| LICS Edits | 104 | 233 | 337 |
| NDC Edits | 2 | 45 | 47 |
| Pharmacy Edits | 0 | 0 | 0 |
| Duplicate Edits | 3 | 0 | 3 |
| CMS Edits | 0 | 0 | 0 |
| Others | 0 | 1 | 1 |
| Total Edits | 383 | 535 | 918 |
| Records Not Accepted On Current File % | 42% | 58% | 100% |

[IMPORT] ← 1425  [EXPORT RESULTS]  [REVIEW IMPORT] ← 1430

Edit Reports Screen

| Home | | | | | SIGN OUT | USER: |
|---|---|---|---|---|---|---|
| PDE Tool: Edits Report | | | | | | |
| Other Details | | | PDE Error Code | LICS Level | Cycle | Fill Date |
| CMS Plan Code: 002<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/01/2009 |
| CMS Plan Code: 001<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/01/2009 |
| CMS Plan Code: 001<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 04/20/2009 |
| CMS Plan Code: 001<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/01/2009 |
| CMS Plan Code: 002<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/13/2009 |
| CMS Plan Code: 002<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/13/2009 |
| CMS Plan Code: 001<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/29/2009 |
| CMS Plan Code: 002<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/21/2009 |
| CMS Plan Code: 001<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/20/2009 |
| CMS Plan Code: 001<br>Claim ID: | Submission Status: NEW<br>Cardholder ID:<br>Last Updated By:    GPS_PDEWMT_004 | | 738 | Member: 0<br>Claim Fill: 0 | Original: 48<br>Current: 48 | 05/27/2009 |

First  <<Prev 20 | Records 1 to 10 (10 total)  | Next 20>>  Last

[EXPORT RESULTS]

Cancel

©2009 MedImpact Healthcare Systems, Inc.

Single Record View Screen

MedImpact®
Delivering • Flexible • Choice

Home  SIGN OUT  USER: RBHALLA

PDE Tool: Single Record View

RECORD DETAILS

| CMS Contract Code: | Original Cycle#: 48 | Plan Year: 2009 |
| CMS Plan Code: 002 | Current Cycle#: 48 | |
| Submission Status: NEW | | |

1710

| Member #: | Group: | Fam. Pos.: 0 |
| Cardholder ID: | Division: | |
| HIC#: | | |

| PDE Edit Code: 705 | Immed. Action. PDE Edit? N | |
| Adj. Deletion Code: | Elig. Update?: N | |

| File Date: 05/06/2009 | LICS Level Member: 0 | Plan Paid Amt.: |
| Claim ID: | LICS Level Claim Fill: 0 | GDCA Amt.: $0.00 |
| Rn#: | LICS Amt.: $0.00 | |
| Pharmacy ID: | | |

COMMENTS

To add a comment click on the link below.
⊟ Add Comment

1733

| Review Status | Review Comment | Entered By | Entered Date |
| --- | --- | --- | --- |
| PENDING CMS | | GPS_PDEWMT_004 | 07/16/2009 |

1730

Cancel

©2009 MedImpact Healthcare Systems, Inc.

FIG. 17

Add Comments Screen

MedImpact®
Delivering • Flexible • Choice

Home  [SIGN OUT]  USER: RBHALLA

PDE Tool: Add Comment

RECORD DETAILS

PDE Edit Code: 705           Original Cycle #:  48
Claim ID:                    Plan Year:         2009

Recent Comment:

COMMENT DETAILS
* = required

*Review Status: REFERRED TO PLAN ▼
*Comment:       Reviewed

[SAVE]  Cancel

©2009 MedImpact Healthcare Systems, Inc.

FIG. 18

| Home | SIGN OUT |
|---|---|
| PDE Tool: Import File | |

\* = required

SELECT A FILE TO IMPORT
To impor a file, click the "BROWSE" button to select a file then click "UPLOAD" below. A comment is also required.

\*Select File: [_____]  [BROWSE] ~1910
\*Comment: [_____]

[UPLOAD] Cancel
  ~1920

FIG. 19

| | A | B | C | D | E | F |
|---|---|---|---|---|---|---|
| 1 | CMS Submitter# | Plan Year | Claim ID | PDE Edit Code | Review Status | Review Comment |
| 2 | | 2009 | 2999999991 | 707 | REFERRED TO PLAN | MARx reflects PBP 001 on DOS |
| 3 | | 2009 | 2999999992 | 707 | REFERRED TO PLAN | MARx reflects PBP 001 on DOS |
| 4 | | 2009 | 2999999993 | 707 | REFERRED TO PLAN | MARx reflects PBP 001 on DOS |
| 5 | | 2009 | 2999999994 | 707 | REFERRED TO PLAN | MARx reflects PBP 001 on DOS |
| 6 | | 2009 | 2999999995 | 707 | REFERRED TO PLAN | MARx reflects PBP 001 on DOS |
| 7 | | 2009 | 2999999996 | 707 | REFERRED TO PLAN | MARx reflects PBP 001 on DOS |
| 8 | | 2009 | 2999999997 | 707 | REFERRED TO PLAN | MARx reflects PBP 001 on DOS |
| 9 | | 2009 | 2999999998 | 707 | REFERRED TO PLAN | MARx reflects PBP 001 on DOS |
| 10 | | 2009 | 2999999999 | 707 | REFERRED TO PLAN | MARx reflects PBP 001 on DOS |
| 11 | | | | | | |
| 12 | | | | | | |

FIG. 20

PDE Tool: File Import Search

* = required

FILE IMPORT SEARCH
To perform a file import search, use the fields below. File Import Status by default shows that the latest submitted files and/or results based on search criteria.

File Name:                    Import Date (yyyy-mm-dd):
File Status:                  Plan Year:
Imported By:

SEARCH 2110 (File Name, File Status, Imported By)
2120 (SEARCH button)

View        File Details                              Import Details           Subm.      Plan
                                                                               Cycle      Year       Totals
VIEW        File Name:                                Imported By:                                    Received:
            File Status:                              Import ID #:                                    Unchanged:
            Entered By:                               Comment:                                        Updated:
            Entered Date:                                                                             Errors:
            Import Date:

2135 (View)
2130 (arrow)

First << Prev 20 | Records 1 to 1 (1 total) | Next 20 >> Last

EXPORT RESULTS

FIG. 21

PDE Tool: File Import Detail

File Name:
File Import Status:
Plan Year:
Import ID#:

Entered By:
Entered Date:
File Uploaded By:
File Uploaded Date:

Total Recs:
Total Updated Recs:
Total Unchanged Recs:
Total Error Recs:

File Import Comments:

| Claim ID | PDE Error Code | Sub Review Status | Sub Review Comment | Import Status | Plan Year | Entered Date | Entered By |
|---|---|---|---|---|---|---|---|
| 29224685 | 716 | REFERRED TO PLAN | | UPDATED | 2009 | | |
| 29224688 | 716 | REFERRED TO PLAN | | UPDATED | 2009 | | |
| 29336923 | 716 | REFERRED TO PLAN | | UPDATED | 2009 | | |
| 29336923 | 716 | REFERRED TO PLAN | | UPDATED | 2009 | | |

FIG. 22

PDE Tool | Home                                        Sign Out | USER: PDETESTUSER@POS09

Please make a selection from the options below.

>> Cycle Summary Report
Generates a summary report for all submitters.

>> Change PDE Cycle Status
Void PDE cycle.

>> Cycle Management
Create PDE Cycle/Version Schedule Load&Extract.

>> File Submission Summary
Get file submission summary for selected submitter.

>> Find File Submissions
Search for file submissions.

>> Find Batch Headers
Search for batch header records.

>> Find PDE Claims
Search for PDE claim records.

The use of this computer program is restricted to terms outlined in the MedImpact employee policy and/or business partner's agreement. Any unauthorized use is strictly prohibited. If you are not an authorized user, disconnect immediately; continued activities are logged and will result in civil and criminal penalties.

©2006 MedImpact Healthcare Systems, Inc.

FIG. 23

* = required

HQ Code: ▢
- or -
CMS Submitter Code: ▢
[SEARCH]  Clear

| CMS Submitter Code | Current Cycle # | Current Cycle Version # | Version Status | From Date | Thru Date | Action | Job Status |
|---|---|---|---|---|---|---|---|
| | 19 | 1 | COMPLETE | 06/01/2007 | 06/30/2007 | [CREATE CYCLE] | DDPS LOADED AT :02/27/2008 13:54:23 |

<< Results 1 to 1 (1 total) >>

FIG. 24

* = required

CMS Submitter Code:
New Cycle #: 19
New Cycle Version #: 1
From Date (mm/dd/yyyy): 07/01/2007 🗓
Thru Date (mm/dd/yyyy): ▢ 🗓

[CREATE NEW CYCLE]  Clear

Cancel

FIG. 25

\* = required

HQ Code: ☐
- or -
CMS Submitter Code: ☐
[SEARCH]  Clear

| CMS Submitter Code | Current Cycle # | Current Cycle Version # | Version Status | From Date | Thru Date | Action | Job Status |
|---|---|---|---|---|---|---|---|
| | 48 | 1 | NEW | 06/01/2009 | 06/30/2009 | [BEGIN LOAD] | CYCLE CREATED AT:07/15/2009 09:18:51 |

<< Results 1 to 1 (1 total) >>

FIG. 26

\* = required

HQ Code: ☐
- or -
CMS Submitter Code: ☐
[SEARCH]  Clear

| CMS Submitter Code | Current Cycle # | Current Cycle Version # | Version Status | From Date | Thru Date | Action | Job Status |
|---|---|---|---|---|---|---|---|
| | 49 | 1 | IN PROGRESS | 06/01/2009 | 06/30/2009 | [BEGIN EXTRACT] | LOAD COMPLETED AT: |

<< Results 1 to 1 (1 total) >>

\* = required

PDE FileHdr Id.: 100000004623  CMS Submitter Code:
File Prefix:                    File Seq: 185            File Header Type:  PROD Batch Count: 7                  Record Count: 7942

Check this box to Zip (compress) the files  ☐

[SUBMIT]

\>> Cancel and return to Previous Screen

FIG. 29

| PDE Tool | Find File Submissions | | | | | | | | | | Home | Sign Out | USER: PDETESTUSER@POS23 |

\* = required

↻ Refresh | Jump to Errors | Jump to Notes

| PDE FileHdr Id: 8000000027 | CMS Submitter Code: | Submitted Date: 08/17/2009 |
|---|---|---|
| File Prefix: | File Seq: 3 | File Header Type: PROD |
| Entered: 08/18/2009 | Entered By: pde_ddps_load.sh | |
| File Status: SUBMITTED | Source: MI | |
| Batch Count: 4 | Record Count: 17 | |
| Accepted Count: 14 | Rejected Count: 2 | Info Count: 1 |

BATCH HEADERS

| Select | Contract Code | Plan Code | Cycle Number | Cycle Version | Status | Plan Year | Entered | Records Count | Accepted Count | Rejected Count | Info Count |
|---|---|---|---|---|---|---|---|---|---|---|---|
| SELECT | | 008 | 503 | 2 | SUCCESS | 2009 | 08/18/2009 | 14 | 11 | 2 | 1 |
| SELECT | | 013 | 503 | 2 | SUCCESS | 2009 | 08/18/2009 | 1 | 1 | 0 | 0 |
| SELECT | | 805 | 503 | 2 | SUCCESS | 2009 | 08/18/2009 | 1 | 1 | 0 | 0 |
| SELECT | | 811 | 503 | 2 | SUCCESS | 2009 | 08/18/2009 | 1 | 1 | 0 | 0 |

ERRORS (click headers to sort) [Flag as Resolved]

| Resolved | Error Source | Error Code | Description | | Resolved By | Resolved Date | Entered Date | Entered By |
|---|---|---|---|---|---|---|---|---|

NOTES [ ☐ Add Note ]

| Created Date | Entered Date | Entered By | Note Text |
|---|---|---|---|

[ FIX IT ] [ CHANGE STATUS ]

>> Top
>> Return to Previous Screen

| PDE Tool | Find Submission Summary | | | Home | Sign Out | USER: PDETESTUSER@POS23 |

*=required

*CMS Submitter Code: [    ]  From Cycle #: [  ] to [  ]

Submitter After: [    ]  Submitter Before: [    ]
(mm/dd/yyyy)  (mm/dd/yyyy)
Entered After: [    ]  Entered Before: [    ]
(mm/dd/yyyy)  (mm/dd/yyyy)

[SEARCH]  Clear

| Expand | File Details | File ID Prefix | File ID Seq # | Submitted | Status |
|---|---|---|---|---|---|
| ⊞ | FILE DETAILS | | 74 | 12/16/2008 | SUBMITTED |
| ⊞ | FILE DETAILS | | 75 | 01/16/2009 | SUBMITTED |
| ⊞ | FILE DETAILS | | 76 | 01/15/2009 | ERROR |

©2006 MedImpact Healthcare Systems, Inc.

| Expand | File Details | File ID Prefix | File ID Seq # | Submitted | Status |
|---|---|---|---|---|---|
| ⊟ | FILE DETAILS | | 75 | 01/16/2009 | SUBMITTED |

| Expand | Batch Details | Seq No | Contract Code | Plan Code | Cycle # | Cycle Version |
|---|---|---|---|---|---|---|
| ⊟ | BATCH DETAILS | 1 | | 006 | 42 | 1 |

| Expand | Batch Details | Seq No | Contract Code | Plan Code | Cycle # | Cycle Version |
|---|---|---|---|---|---|---|
| ⊟ | BATCH DETAILS | 2 | | 801 | 42 | 1 |

| Expand | Batch Details | Seq No | Contract Code | Plan Code | Cycle # | Cycle Version |
|---|---|---|---|---|---|---|
| ⊟ | BATCH DETAILS | 3 | | 802 | 42 | 1 |

| Find Claims | Error Source | Claim Count | Error Count | Resolved Count |
|---|---|---|---|---|
| FIND CLAIMS | CMS | 15 | 15 | 14 |

FIG. 32

⚙ Refresh | Jump to Errors | Jump to Notes

| CMS Contract Code: | | CMS Plan Code: | | CMS Plan Year: | 2008 | |
|---|---|---|---|---|---|---|
| Cycle Number: | 50 | Cycle Version: | 1 | Seq No: | 1 | |
| Entered By: | PDE_LOAD | Entered: | 08/17/2009 | Status: | ERROR | |
| Records Count: | 18 | Accepted Count: | 0 | Rejected Count: | 0 | Info FB Count: 0 |

ERRORS (Click headers to sort) [ Flag as Resolved ]

| Resolved | Error Source | Error Code | Description | Resolved By | Resolved Date | Entered Date | Entered By |
|---|---|---|---|---|---|---|---|
| ☐ | POP | 229 | CONTRACT NUMBER IS MISSING IN HEADER. | | | 08/17/2009 | PDE_LOAD |
| ☐ | POP | 230 | CONTRACT NUMBER DOES NOT MATCH NUMBER ASSIGNED BY CMS. | | | 08/17/2009 | PDE_LOAD |
| ☐ | POP | 233 | PBP ID IS MISSING. | | | 08/17/2009 | PDE_LOAD |
| ☐ | POP | 234 | PBP IS NOT VALID FOR THE CONTRACT ID. | | | 08/17/2009 | PDE_LOAD |

NOTES [ ☐ Add Note ]

| Created Date | Entered Date | Entered By | Note Text |
|---|---|---|---|
| | | | |

[ FIX IT ]  [ CHANGE STATUS ]

FIG. 33

| PDE Tool | PDE Batch Header - Change Status | Home | Sign Out | USER: ADACUT@POS04 |

*=required

CMS Contract Code: CMS Plan Code: CMS Plan Year: 2008
Cycle Number: 50 Cycle Version: 1 Seq No: 1

Status: ERROR

To change the status, use the pulldown and click "Submit" below.

*Change Status to: [EXCLUDE ▼]
[SUBMIT]

Cancel

©2006 MedImpact Healthcare Systems, Inc.

FIG. 34

PDE Tool | Find PDE Claims

*=required

CMS Submitter Code: [      ]
- OR -
Claim ID: [      ]

From Cycle #: [  ] to [  ]         PDE Claim ID: [      ]
Cycle Version: [      ]             CMS Contract Code: [      ]
Status: [      ]                     CMS Plan Code: [      ]
Plan Year (yyyy): [      ]
Rx #: [      ]

HIC #: [      ]                      Card Holder ID: [      ]

Error Source: [      ]               Error Code: [      ]

From Date of Service: [      ]      To Date of Service: [      ]
(mm/dd/yyyy)                         (mm/dd/yyyy)
From Date Paid: [      ]            To Date Paid: [      ]
(mm/dd/yyyy)                         (mm/dd/yyyy)

Exclude Void Versions: [No ▼]

[SEARCH]  [CLEAR]

FIG. 35

| View | Edit | Contract Code | Plan Code | Cycle Number | Cycle Version | Claim Status | Batch Status | Version Status | Rx #: | POS Claim ID | HIC # | Date of Service |
|---|---|---|---|---|---|---|---|---|---|---|---|---|
| VIEW | EDIT | | 1 | 1001 | 1 | FB ERROR | SUCCESS | COMPLETE | | | | 04/02/2009 |
| VIEW | EDIT | | 1 | 1001 | 1 | FB ERROR | SUCCESS | COMPLETE | | | | 04/09/2009 |
| VIEW | EDIT | | 1 | 1001 | 1 | FB ERROR | SUCCESS | COMPLETE | | | | 04/09/2009 |
| VIEW | EDIT | | 1 | 1001 | 1 | FB ERROR | SUCCESS | COMPLETE | | | | 04/09/2009 |
| VIEW | EDIT | | 1 | 1001 | 1 | FB ERROR | SUCCESS | COMPLETE | | | | 04/13/2009 |
| VIEW | EDIT | | 2 | 1001 | 1 | FB ERROR | SUCCESS | COMPLETE | | | | 04/06/2009 |
| VIEW | EDIT | | 2 | 1001 | 1 | FB ERROR | SUCCESS | COMPLETE | | | | 04/06/2009 |
| VIEW | EDIT | | 2 | 1001 | 1 | FB ERROR | SUCCESS | COMPLETE | | | | 04/13/2009 |
| VIEW | EDIT | | 2 | 1001 | 1 | FB ERROR | SUCCESS | COMPLETE | | | | 04/13/2009 |

EXPORT RESULTS

FIG. 36

SYSTEM AND METHOD FOR WEB-BASED CLAIM MANAGEMENT

CROSS REFERENCE TO RELATED APPLICATION

This application claims the benefit of and priority to U.S. Provisional Application No. 61/271,964, filed Jul. 28, 2009, entitled SYSTEM AND METHOD FOR WEB-BASED CLAIM MANAGEMENT, the entire content of which is incorporated herein by reference.

BACKGROUND

Field

The present disclosure generally is related to medical claim management, including web-based management of claims for submission to governmental agencies.

Background

Medicare Part D is a federal program that went into effect Jan. 1, 2006, which subsidizes the costs of prescription drugs for Medicare beneficiaries in the United States. In order for private Medicare Part D plan sponsors to be reimbursed based on this subsidization, health insurers regularly submit claims to the Centers for Medicare and Medicaid Submission (CMS) containing detailed reporting of pharmacy transactions.

In order to process the multitude of claims, CMS requires that the claims be submitted in a specific format called a Prescription Drug Event (PDE) file. A single PDE file may contain thousands of claim records, with each record corresponding to a single claim. When a PDE file, or a claim record of the file, does not meet the stringent CMS requirements, CMS rejects the claim and associates the rejected claim with a PDE "edit" code. PDE edits can occur for a number of reasons, including incomplete information, incorrect information, or duplicate information.

After receiving a PDE file from a claimant, CMS returns a Drug Data Processing System (DDPS) transaction validation response file (a "DDPS file"), which indicates, among other things, which claims in the PDE file were in error. The DDPS file usually includes claim numbers and an edit code associated with the claim number that is associated with the reason for the edit.

For example, CMS may reject a PDE claim because CMS has no record of the beneficiary being enrolled in Part D on the date of service (edit code 705), because the beneficiary is not eligible for a Low Income Cost-sharing Subsidy (LICS) reimbursement (edit code 715), because the indicated prescription is not covered by Medicare Part D (edit code 738), or because of internal CMS issues (edit code 999).

Typically, the various individual Medicare Part D plan sponsors generate their own files and send these files to CMS. However, numerous problems can occur when generating PDE files, resulting in PDE edits from CMS. From the perspective of the various Medicare Part D plan sponsors, PDE edits represent lost revenue from CMS. Further, PDE errors can affect the reputation, business model, credibility, and competitive posture of Part D plan sponsors. Accordingly, minimization of PDE error rate is an important factor in the overall design, function, and profitability of any Part D plan sponsor.

Generally, disclosed herein are systems for managing the claim process including systems for generating more accurate PDE files and for simplifying the tracking and correction of PDE edits.

SUMMARY

The systems and methods described herein each have several aspects, no single one of which is solely responsible for its desirable attributes. Without limiting the scope of this disclosure as expressed by the claims which follow, its more prominent features will now be discussed briefly. After considering this discussion, and particularly after reading the section entitled "Detailed Description" one will understand how the sample features described herein provide advantages that include the generation of more accurate formatted claim files and the facilitation of tracking and correcting errors in claims. Although much of the description herein is directed to the generation, correction, and management of prescription drug claims submitted as part of Medicare Part D, one of ordinary skill in the art will appreciate that the aspects disclosed herein are equally applicable to the generation, correction, and management of other data.

One aspect relates to methods of generating formatted claim files. The methods can include, for example, receiving claim information at a server from a user via a web-based interface, receiving eligibility information at the server from the user via the web-based interface, determining financial information based at least in part on a portion of the received claim information and a portion of the eligibility information, and generating a formatted claim file based at least in part on the portion of the claim information, the portion of the eligibility information, and the financial information. The methods further can include, for example, transmitting the formatted claim file to the user via the web-based interface. The formatted claim file can be a Prescription Drug Event (PDE) file. The methods further can include transmitting the PDE file to the Centers for Medicare and Medicaid Submission (CMS). The claim information can be, for example, indicative of plurality of pharmaceutical transactions. The eligibility information can be, for example, indicative of Medicare beneficiary status. The methods further can include, for example, validating the determined financial information.

Another aspect relates to systems for generating formatted claim files. The systems can include for example, a receiver configured to receive claim information and eligibility information from a user via a web-based interface, and a processor configured to determine financial information based at least in part on a portion of the received claim information and a portion of the eligibility information, wherein the processor is further configured to generate a formatted claim file based at least in part on the portion of the claim information, the portion of the eligibility information, and the additional information. The systems further can include, for example, a memory configured to store at least one of the claim information, the eligibility information, the additional information, or the formatted claim file. The memory can include, for example, a web-accessible database. The systems further can include, for example, a transmitter configured to transmit the formatted claim file to the user via the web-based interface. The formatted claim file can be, for example, a Prescription Drug Event (PDE) file, and in some aspects the systems further can include, for example, a transmitter configured to transmit the PDE file to the Centers for Medicare and Medicaid Submission (CMS). The processor can be further configured to validate the determined financial information.

Another aspect relates to methods of managing claims. The methods can include, for example, storing a plurality of claim objects in a database, each claim object associated with a unique claim number, receiving rejection data indicative of a plurality of claim numbers and a plurality of respective edit codes, each edit code indicative of a rejection of a claim, parsing the rejection data so as to generate a plurality of claim object update data, each claim object update data associated with a stored claim object and indicative of the respective edit code of the unique claim number associated with the stored claim object, updating the associated stored claim objects based on the claim object update data to indicate the reception of the respective edit code, receiving a query via a web-based interface, and responding to the query based on the updated claim objects stored in the database. The query can indicate, for example, an edit code and the response to the query can contain, for example, data indicative of the stored claim objects updated to indicate the reception of the edit code. The rejection data can be received, for example, at a particular time and wherein updating the associated stored claim objects may include updating the associated stored claim objects to indicate the reception of the respective edit code at the particular time. The query can indicate, for example, a particular time range and the response to the query may contain, for example, data indicative of the stored claim objects updated within the time range. The stored claim objects may be associated, for example, with a status, wherein the query indicates a particular status, and wherein the response to the query contains data indicative of the stored claim objects associated with the particular status. The status can be, for example, rejected or accepted. The methods further can include, for example, modifying the claim object based on information received via the web-based interface. The modifying the claim object may include, for example, adding comment data to the claim object.

Another aspect relates to systems for managing claims. The systems may include, for example, a web-accessible database configured to store a plurality of claim objects, each object associated with a unique claim number, a receiver configured to receive data indicative of a plurality of claim numbers and plurality of respective edit codes, each edit code associated with a claim rejection, a processor configured to parse the received data into a plurality of claim object update data, each claim object update data associated with a stored claim object and indicative of the respective edit code of the unique claim number associated with the stored claim object, wherein the processor is further configured to update the associated stored claim objects based on the claim object update data to indicate the reception of the respective edit code, wherein the receiver is further configured to receive a query via a web-based interface, wherein the processor is further configured to generate a response to the query based on the claim objects in the database, and a transmitter configured to transmit the response to the query.

Yet another aspect relates to systems for managing PDE files, which can include, for example, a system for generating PDE files, a system for submitting the PDE files to CMS, a system for receiving and organizing DDPS files from CMS, and a web-based system for tracking and presenting PDE edits in a queryable format. The system further can include, for example, a web-based system for identifying trends in the PDE edits over time. The web-based system for tracking and presenting the PDE edits can present an aged rolling history format of the PDE edits. The system for generating PDE files can receive claim and eligibility data, for example, from an internal source. The system for generating PDE files can receive claim and eligibility data, for example, from an external $3^{rd}$ party source. The web-based system for tracking and presenting PDE edits can track PDE edits, for example, by comparing the PDE files submitted to CMS and the DDPS files received from CMS. The web-based system for tracking and presenting PDE edits can include, for example, a web-based user interface for querying the PDE edits. The web-based user interface can present the PDE edits in an aged format, for example. The web-based user interface can present the PDE edits together with user edited comments, for example. The web-based user interface can present the PDE edits together with PDE edit codes, for example. The PDE edits can be, for example, tracked, and categorized as being new or resubmitted. The web-based user interface may be configured such that a user can search the PDE edits, for example. The PDE edits can be searched by edit type, for example. The PDE edits can be searched by edit age, by data field, and the like, for example. The data field may include, for example, at least one of a claim identification field, a member identification field, an edit code field, a prescription field, a date of service field, and the like. The system for generating PDE files may be configured to selectively void PDE files before submission. The system for submitting the PDE files to CMS may be configured to selectively skip one or more submission periods.

Yet another aspect relates to methods of managing PDE files, which methods can include, for example, receiving claim data into a computer system for generating PDE files, receiving eligibility data into a computer system for generating PDE files, generating PDE files from the claim and eligibility data received into the computer system for generating PDE files, submitting the PDE files to CMS, receiving DDPS files from CMS, tracking PDE edits by comparing the PDE files submitted to CMS and the DDPS files received from CMS, categorizing the PDE edits as being new or resubmitted, and presenting the PDE edits in a queryable format on a web-based interface. The methods further can include, for example, aging the PDE edits; and presenting the PDE edits as a compilation of all edits for a given claim. The methods further can include, for example, querying the web-based interface to present the PDE edits by edit type. The methods further can include, for example, querying the web-based interface to present the PDE edits by edit age. The methods further can include, for example, querying the web-based interface to present the PDE edits by data field. The data field can include, for example, at least one of a claim identification field, a member identification field, an edit code field, a prescription field, a date of service field, and the like. The claim data and eligibility data may be received, for example, from an internal source. The claim data and eligibility data may be received, for example, from an external $3^{rd}$ party source. The methods further can include, for example, inputting user-edited comments associated with the PDE edit fields. The methods further can include, for example, presenting a rolling history associated with each of the PDE edits.

Another aspect relates to facility networks for managing PDE files. The networks can include, for example, at least one Medicare Part D claim processing facility and a Medicare Part D PDE file generation and management computer facility, wherein the Medicare Part D claim processing facility comprises a Medicare Part D claim processing computer system and a patient eligibility determination computer system and wherein the Medicare Part D PDE file generation and management computer facility comprises a Medicare Part D claim loading and validation system in communication with the Medicare Part D claim processing system, a Medicare Part D eligibility load and validation system in communication with the Medicare Part D eligibility determination computer system, a PDE file generating system in communication with the claim loading and validation system and the eligibility load and validation system, wherein the PDE file generating system compares validated claims and validated eligibility determinations to generate PDE files, a PDE file transmission system for submitting PDE files from the Medicare Part D PDE file generation and management computer facility to CMS, a DDPS file receiving system for receiving DDPS files from CMS, and a web-based system for tracking and presenting PDE edits in a queryable format. The Medicare Part D PDE file generation and management computer facility further may include, for example, a web-based system for tracking and presenting PDE file edits in an aged rolling history format. The at least one Medicare Part D claim processing facility may be, for example, an external $3^{rd}$ party facility. The at least one Medicare Part D claim processing facility may include, for example, a plurality of external $3^{rd}$ party facilities, each including, for example, a Medicare Part D claim processing computer system, and a patient eligibility determination computer system. The Medicare Part D claim processing facility may be, for example, an internal facility. The at least one Medicare Part D claim processing facility further may include, for example, an operator workstation having a web-based interface for querying the PDE edits tracked by the web-based system for tracking and presenting PDE edits. The Medicare Part D PDE file generation and management computer facility further may include, for example, an operator workstation having a web-based interface for querying the PDE edits tracked by the web-based system for tracking and presenting PDE edits.

One aspect is a method of generating formatted claim files, the method comprising receiving claim information from a user via a web-based interface, receiving eligibility information from the user via the web-based interface, determining additional information based at least in part on a portion of the received claim information and a portion of the eligibility information, and generating a formatted claim file based at least in part on the portion of the claim information, the portion of the eligibility information, and the additional information. Another aspect further includes transmitting the formatted claim file to the user via the web interface.

One aspect is a method of managing claims, the method comprising storing a plurality of claim objects in a database, each claim object associated with a unique claim number, receiving a list of claim numbers, each claim number associated with an edit code, revising the respective claim objects associated with the listed claim numbers to indicate the reception of the edit code associated with the claim number, receiving a query via a web-based interface, and responding to the query based on the claim objects in the database. Another aspect further includes modifying the claim object based on information received via the web-based interface.

Another aspect is a method of loading claim files into an adjudication system, the method comprising receiving claim error related files at a server from a user via a web-based interface, validating the claim error related files for data integrity, recording errors that occur during validation of the claim error related files in a log, parsing the claim error related files for claim records, comparing the parsed claim records to existing claim records in the adjudication system, assigning a claim identification to the parsed claim records based on the comparison, and storing the claim records in the adjudication system.

Still some aspects relate to methods for managing prescription claim reimbursement. The methods can include any of the methods described herein alone or combined. Also, some aspects relate to multifunctional systems for prescription claim management, which systems can include any of the systems or methods described herein, alone or in any combination.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, not to be considered limiting of its scope, the disclosure will be described with additional specificity and detail through use of the accompanying drawings.

FIG. 6 is a screenshot of an example of a dashboard screen.

FIG. 7 is a screenshot of an example of a search page screen.

FIG. 8 is a screenshot of an example of a record page.

FIG. 10 is a screenshot of an example of a LICS Report.

FIG. 11 is a screenshot of an example of a PDE Summary Report.

FIG. 14 is a screenshot of an example of a dashboard screen.

FIG. 15 is a screenshot of an example of a report screen.

FIG. 16 is a screenshot of an example of a search page screen.

FIG. 17 is a screenshot of an example of a record page.

FIG. 18 is a screenshot of an example of an add comments page.

FIG. 19 is a screenshot of an example of an import file selection page.

FIG. 20 is a screenshot of an example of an import file.

FIG. 21 is a screenshot of an example of an import file search page.

FIG. 22 is a screenshot of an example of a claim import detail page.

FIG. 23 is a screenshot of an example of a home page.

FIG. 24 is a screenshot of an example of a cycle management page.

FIG. 25 is a screenshot of an example of a create new cycle page.

FIG. 26 is a screenshot of an example of a load cycle page.

FIG. 27 is a screenshot of an example of a extract cycle page.

FIG. 28 is a screenshot of an example of a find file submissions page.

FIG. 29 is a screenshot of an example of a file submission posting page.

FIG. 30 is a screenshot of an example of a file submission page.

Figure 31:
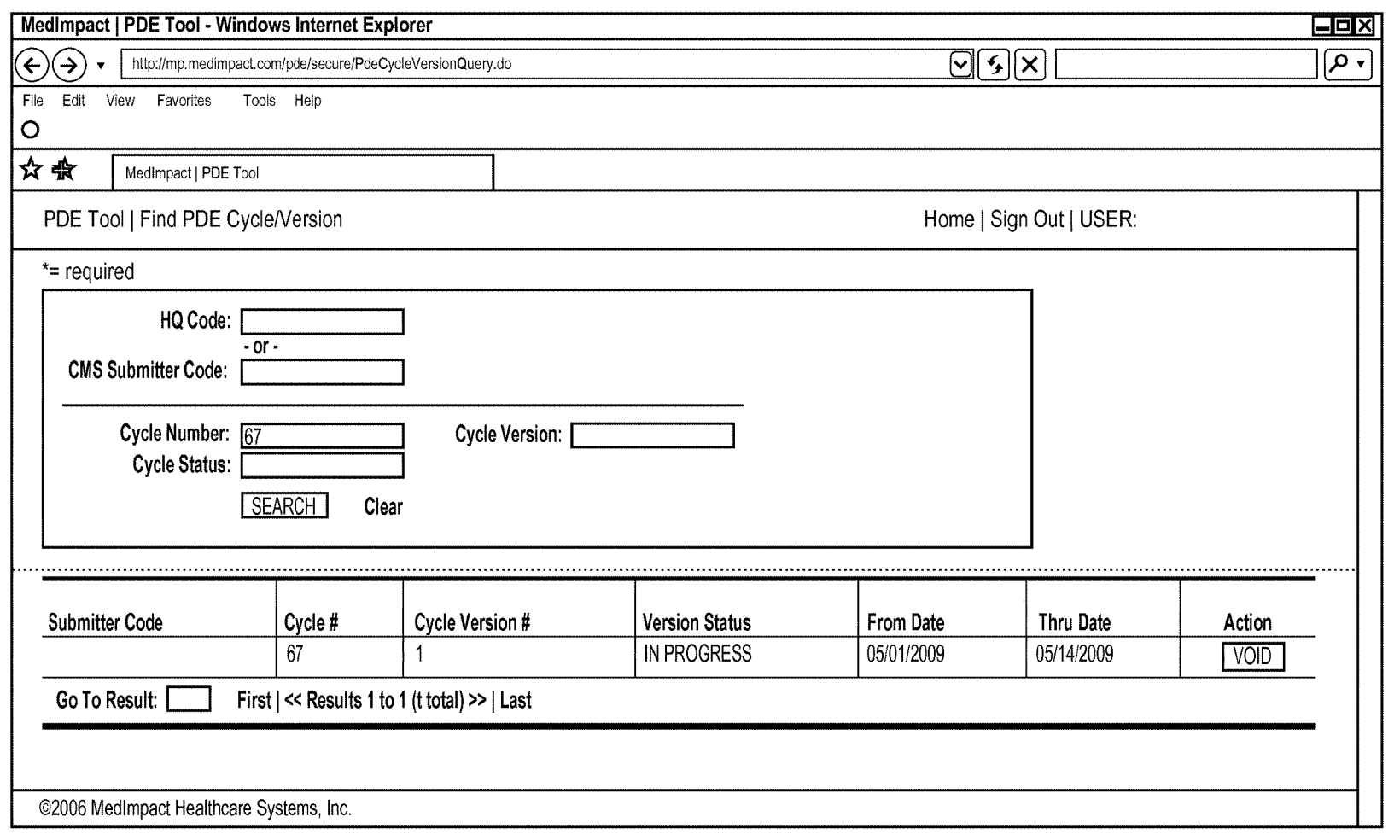

FIG. 31 is a screenshot of an example of a find cycle page with an option to void a cycle.

FIG. 32 is a screenshot of an example of a file submission summary page.

FIG. 33 is a screenshot of an example of a batch header page.

FIG. 34 is a screenshot of an example of a batch header change status page.

FIG. 35 is a screenshot of an example of a find claims page.

FIG. 36 is a screenshot of an example of a claim results page.

DETAILED DESCRIPTION

Figure 1A:
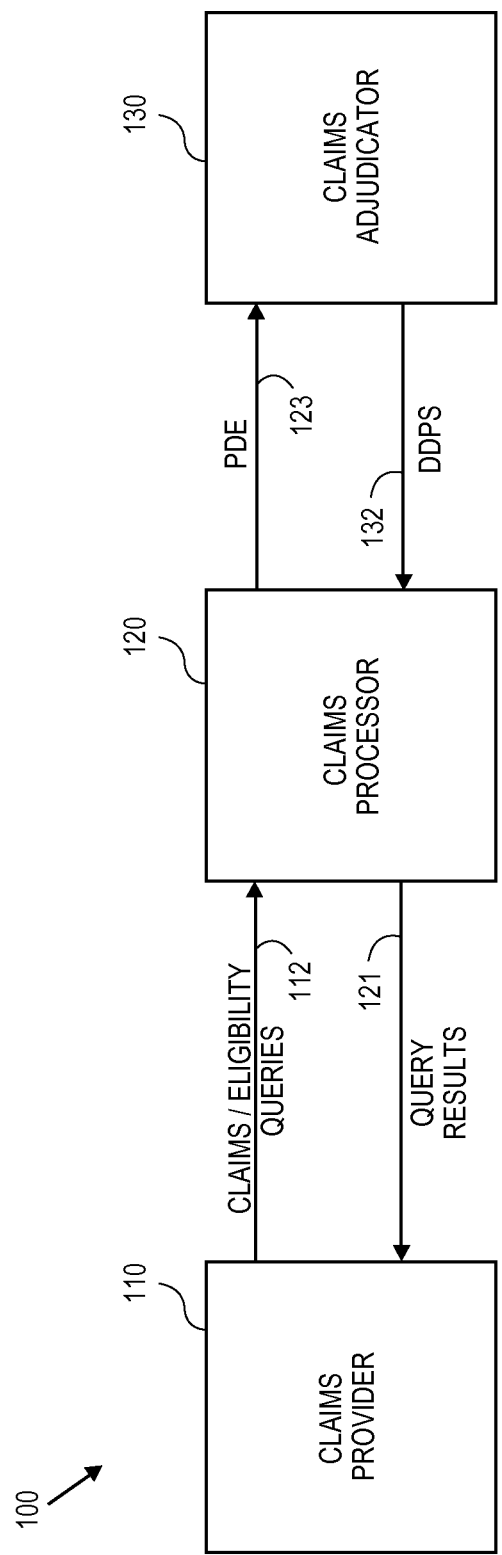
FIG. 1A is a block diagram of an example of a claim processing system.

The following detailed description is directed to certain specific aspects. However, the aspects described herein can be embodied in a multitude of different ways, for example, as defined and covered by the claims. It should be apparent that the aspects herein may be embodied in a wide variety of forms and that any specific structure, function, or both being disclosed herein is merely representative. Based on the teachings herein one skilled in the art should appreciate that an aspect disclosed herein may be implemented independently of any other aspects and that two or more of these aspects may be combined in various ways. For example, a system or apparatus may be implemented or a method may be practiced using any number of the aspects set forth herein. In addition, such a system or apparatus may be implemented or such a method may be practiced using other structure, functionality, or structure and functionality in addition to or other than one or more of the aspects set forth herein.

Similarly, methods disclosed herein may be performed by one or more computer processors configured to execute instructions retrieved from a computer-readable storage medium. A computer-readable storage medium stores information, such as data or instructions, for some interval of time, such that the information can be read by a computer during that interval of time. Examples of computer-readable storage media are memory, such as random access memory (RAM), and storage, such as hard drives, optical discs, flash memory, floppy disks, magnetic tape, paper tape, punch cards, and Zip drives.

Introduction

Typically, the various individual Medicare Part D plan sponsors or their internal claims processing departments generate their own Prescription Drug Event (PDE) files and send these files to the Centers for Medicare and Medicaid Submission (CMS). The PDE generation and submission process requires the handling, calculating, and formatting of large amounts of information. As mentioned above, numerous problems can occur when generating PDE files, resulting in PDE edits from CMS. From the perspective of the claimant, PDE edits represent lost revenue. Common edits can include errors related to enrollment discrepancies due to members being assigned to an incorrect Plan Benefit Package (PBP) or due to having an incorrect Low Income Cost-share Subsidy (LICS).

Some aspects disclosed herein are systems and methods for generating more accurate PDE files from claim information. The systems and methods result in PDE files with surprisingly low error rates. An example of a process of generating PDE files performed by such a system is described below with respect to FIG. 4. In one embodiment, the system receives claim information from a user over a web-based interface and returns validated PDE files based on the claim information to the user over the same interface. One embodiment of the web-interface is described with respect to FIGS. 6-11. Another embodiment of the web-interface is described with respect to FIGS. 12-22. In another embodiment, the system receives claim information from a user over the web-based interface and submits validated PDE files based on the claim information to CMS on the user's behalf, for example as shown in FIG. 23-36.

In one embodiment, the system advantageously centralizes the generation of PDE files (and correction of PDE files as described below) for several different Medicare Plan D plan sponsors of the user at one central facility. The user can identify edits common to different plans and implement solutions to correct the edits in a timely manner. The centralized system at least partially automates the generation of PDE files such that up-to-date information is used in the generation of the PDE files. In some aspects, the systems and methods described herein may be configured to minimize the number of errors by detecting potential errors. For example, the systems and methods can determine PDE fields based upon real-time member and accumulator information as outlined in Table 1. In one embodiment, the system calculates additional fields and error checks them for financial and format errors before creation of PDE file data, thereby reducing or eliminating the total amount of PDE files that could be rejected by CMS and allowing internal processes to fix these claims before submission to CMS.

While it is certainly desirable to submit error-free PDE files, errors inevitably occur. The errors are reported by CMS via a report called a Drug Data Processing System (DDPS) transaction validation response file (DDPS). Unfortunately, the DDPS files include limited information and the files present the information in a manner that requires great effort on behalf of the submitter to efficiently manage and correct the errors. For example, DDPS files typically do not present the errors in a format that enables a user to quickly identify PDE edits by edit type or by the age of the edit. This is further complicated by the fact that a single claim may have more than one error. It is typically not easy to isolate edits by edit type. As a result, many edits are simply re-submitted without ever being reviewed, and continue to reject in subsequent cycles. That coupled with large volume of claims and errors makes the error correction process extremely complicated.

Prompt and efficient error resolution can be very important to the insurance plans. For example, if errors are not corrected within a certain period of time, the insurer may be precluded from ever being reimbursed. Also, some errors may be incurable, for example, the insured may not be eligible for Medicare Part D, which means the insurer will not be able ever to be reimbursed for the claim. Identification of such an error early can prevent continued loss by the insurer caused by the insured continuing to receive medications under the Medicare Part D plan when not entitled to do so. Timely recognition and correction of such errors can save large amounts of money for the insurers.

Thus, some embodiments relate to systems and methods for managing the error correction process and for resubmitting PDE files to CMS. Resubmission of a corrected PDE can result in the claimant receiving the subsidy which it is due.

Therefore, another aspect disclosed herein is a system for simplifying the tracking and correction of edits. An example of a process of managing claims performed by such a system is described below with respect to FIG. 5. In one embodiment, the system receives a DDPS file which simply indicates which claim records of a transmitted PDE file are in error and the reasons for the error. The system formats and accumulates this information in a web-accessible database which the user can access, query, and modify via the web-based interface.

There may be significant delays between when an edit is identified by CMS and when it is reported to the user in a format the user can use to resolve the edit. Advantageously, the centralized system can significantly shorten this delay, preferably allowing user access to the web-based interface to see the most current accumulated and formatted data. For example, the system can provide the user with access to the most current, completed PDE cycle information.

The accumulation and formatting of the data allows the user to observe the history of claim submissions and rejections and the history of particular claims. This information allows the user to identify trends in edit code frequency or if a particular claim record has been repeatedly edited for the same reason for a number of cycles. The web-based interface also provides searching and reporting features to allow the user to quickly focus on the rejected claims by resolution priority, thereby saving time which can be better spent on resolving errors. For example, a user can use the search feature of the system to find certain edits that occur frequently or that have severe financial repercussions for the user.

The web-based interface allows modification of claim records. For example, the user can add comments to mark errors that have been resolved, are in the process of being resolved pending action by a third party, or to assign responsibility to correct errors to particular entities.

Once a user has identified an error, the source of the error, and how to resolve the error, the user can revise internal claim information for resubmission to the system or modify the claim information stored on the database via the web-based interface. The system recognizes the new information and uses this new information in subsequent PDE file generation and submission to CMS.

Thus, some embodiments described herein generally relate to multifunctional systems for managing prescription claim generation, submission, and correction. The systems may include a variety of aspects which allow the user to efficiently receive reimbursement for claims. Claims which are accepted by CMS result in reimbursement for the claimant. Claims which are rejected by CMS represent lost revenue for the claimant. In order to maximize the number of accepted claims and minimize the number of rejected claims, the systems can provide, for example, at least two aspects. A front-end aspect is the generation of more accurate PDE files for submission. A back-end aspect is the accumulation and formatting of information received from CMS to facilitate the correction of PDE errors. Both of these aspects can work in tandem to minimize lost revenue for the claimant.

System Overview

Figure 2:
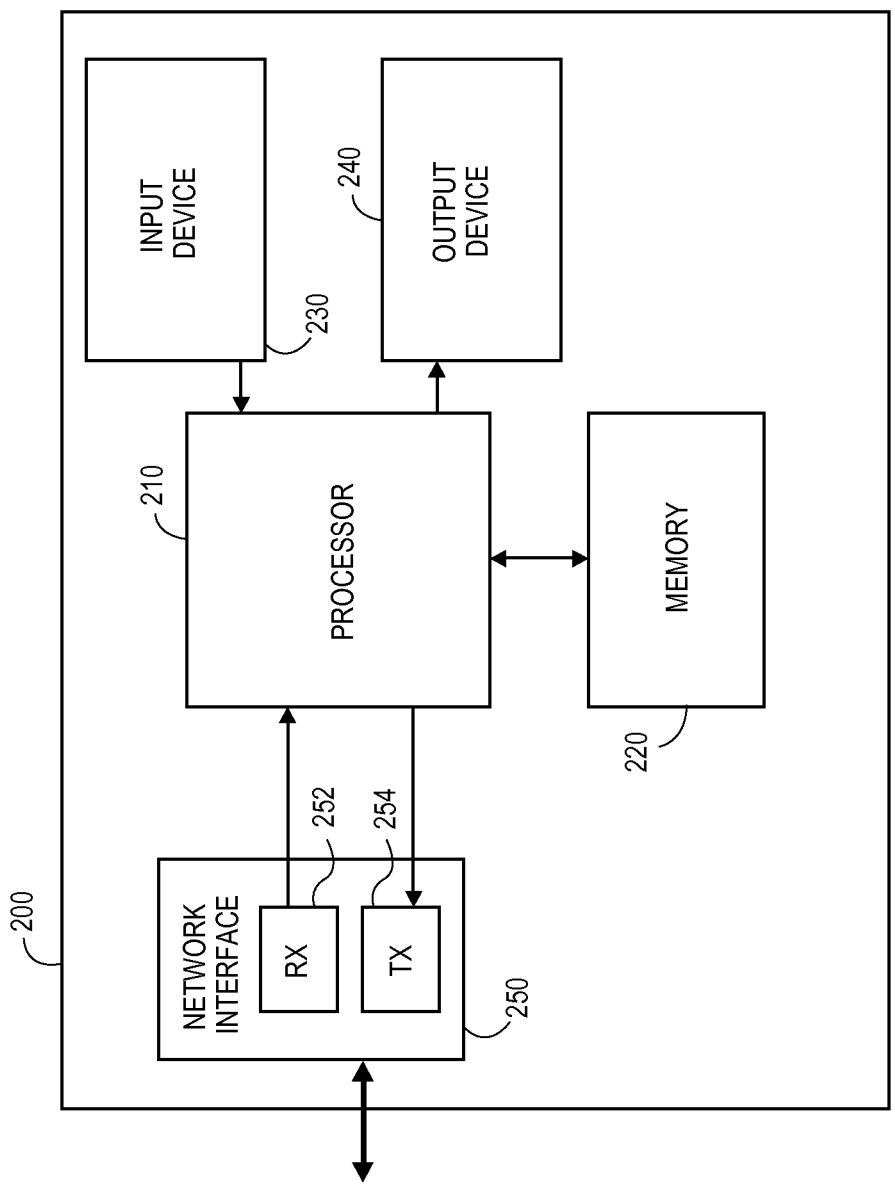
FIG. 2 is a block diagram of an example of a claims management system.

FIG. 1A is a block diagram of a claim system illustrating some examples of interactions between various components. The system 100 includes a claims provider 110, such as a Medicare Part D plan sponsor, a claims processor 120, and claims adjudicator 130, such as CMS. An example of the internal components of the claims processor 120 is shown in FIG. 2. In one embodiment, the claims processor 120 provides a web-based interface to the claims provider 110 over a forward communication link 112 and a reverse communication link 121. The claims provider 110 transmits information to the claims processor 120 over the forward communication link 112. This information can include, for example, registration information, login information, claim information, eligibility information, search queries, report requests, or other data as described with respect to FIGS. 3 and 4 below. The reverse communication link 121 can be used by the claims processor 120 to transmit information to the claims provider 110. This information can include reporting the receipt of information from the claims adjudicator 130 or responding to search queries or report requests.

Based on the available data, the claims processor 120 generates a specially formatted file for submission to the claims adjudicator 130. In one embodiment, the claims processor 120 generates a PDE file, as set forth by CMS. The claims processor 120 can perform a variety of validation checks on the data to ensure that the data is accurate and complete prior to the submission of the formatted file to the claims adjudicator 130. The claims processor 120 transmits the formatted file to the claims adjudicator 130 over a forward communication link 123. In one embodiment, the claims provider 110, claims processor 120, and claim adjudicator 130 are all connected via a network, including Internet Protocol networks such as the Internet. Thus, it is to be appreciated that the communications links 112, 121, 123, and 132 can be representative of the communication functionality rather than physical connections.

The claims adjudicator 130 analyzes the formatted file for errors and edits non-compliant portions of the file. For example, the claims adjudicator 130 can edit the formatted file by rejecting portions corresponding to non-covered claims. The claims adjudicator 130 returns, via a reverse communication link 132, a response file indicating which of the claims contained in the formatted file have been accepted, accepted with minor modifications, or rejected. In one embodiment, the response file further includes information about the claims which have been rejected by associating an edit code with the associated claim.

The claims processor 120 receives the response file from the claims adjudicator 130, extracts relevant information regarding the claims, and stores it in a database. This database can be accessed by the claims provider 110 via forward communication link 112 and reverse communication link 121 in order to resolve the errors that have occurred.

Figure 1B:
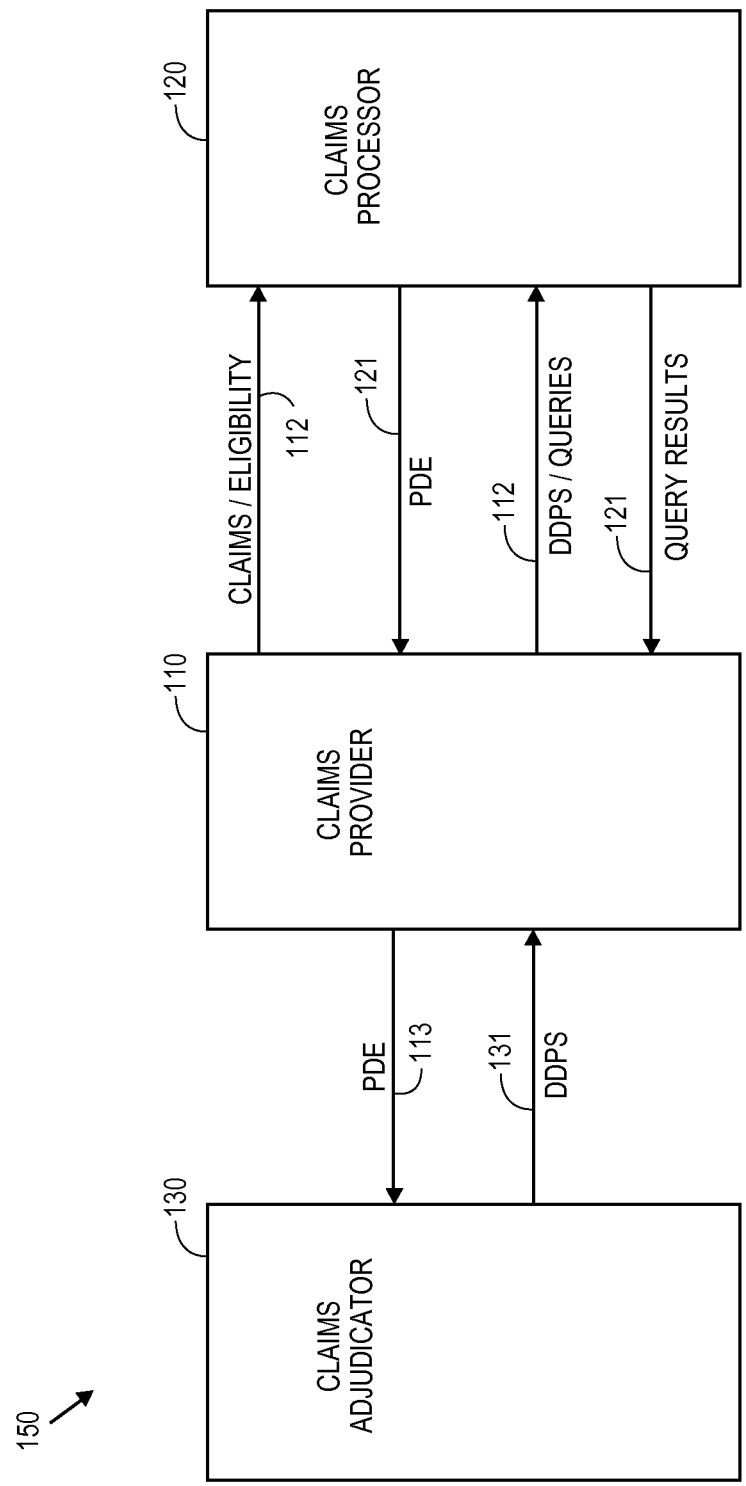
FIG. 1B is a block diagram of another example of a claim processing system.

FIG. 1B is a block diagram of an example of an embodiment of a claim system. In the system 150 illustrated in FIG.

1B, the claims provider 110 submits claims information and eligibility information, and potentially other information, as described above with respect to FIG. 1A over the forward communication link 112 to the claims processor 120. Rather than submitting a specially formatted file (e.g., a PDE file) to the claims adjudicator 130 as in the system 100 of FIG. 1A, the claim processor 120 in FIG. 1B transmits the formatted file to the claims provider 110 over reverse communication link 121.

The claims provider 110 can submit this formatted file to the claims adjudicator 130 over a forward communication link 113 and receive a response file over a reverse communication link 131. In one embodiment, the claims provider forwards the response file to the claims processor for querying.

FIG. 2 is a functional block diagram of an example of a claims management system that can be utilized by the claims processor of FIG. 1, for example. The claims management system 200 includes a processor 210 in data communication with a memory 220, an input device 230, and an output device 240. The processor is further in data communication with a network interface 250, which includes a receiver 252 and a transmitter 254. Although described separately, it is to be appreciated that functional blocks described with respect to the claims management system 200 need not be separate structural elements. For example, the processor 210 and memory 220 may be embodied in a single chip. Similarly, the processor 210 and network interface 250 may be embodied in a single chip. Likewise, the receiver 252 and transmitter 254 may be embodied in a single chip.

The processor 210 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 210 may be configured to, among other things, generate more complete and accurate PDE files based on the information stored in the memory 210 or received via the receiver 252 of the network interface 250. The processor 210 also may be configured to process data contained in received DDPS files and to store the processed data in the memory 210 or transmit the processed data via the transmitter 254 of the network interface 250.

The processor 210 is coupled, via one or more buses, to read information from or write information to memory 220. The processor may additionally, or in the alternative, contain memory, such as processor registers. The memory 220 can include processor cache, including a multi-level hierarchical cache in which different levels have different capacities and access speeds. The memory 220 can also include random access memory (RAM), other volatile storage devices, or non-volatile storage devices. The storage devices can include hard drives, optical discs, such as compact discs (CDs) or digital video discs (DVDs), flash memory, floppy discs, magnetic tape, and Zip drives.

The processor 210, in conjunction with software stored in the memory 220 executes an operating system, such as, for example, Unix or Solaris 5.10. The processor 210 also executes software applications stored in the memory 220. For example, the functionality for generating PDE files based on claim information can be programmed as software stored in the memory 220. In one non-limiting embodiment, the software comprises, for example, Unix Korn shell scripts. In other embodiments, the software can be programs in any suitable programming language known to those skilled in the art, including, for example, C++ and Java.

In one embodiment, the memory 220 may include software for operating the claims management system 200 as a web server, such as for example, the software provided by Apache and Tomcat. In one embodiment, the memory 220 includes a web-accessible database, that is, a database which is accessible via the network interface 250. Software stored in the memory 220, such as for example, Oracle 10 g, provides database services to the processor 210 and to users of the claims management system 200.

The processor 210 is also coupled to an input device 230 and an output device 240 for, respectively, receiving input from and providing output to, a system administrator of the claims management system 200. Suitable input devices include, but are not limited to, a keyboard, buttons, keys, switches, a pointing device, a mouse, a joystick, a remote control, an infrared detector, a video camera (possibly coupled with video processing software to, e.g., detect hand gestures or facial gestures), a motion detector, and a microphone (possibly coupled to audio processing software to, e.g., detect voice commands). Suitable output devices include, but are not limited to, visual output devices, including displays and printers, audio output devices, including speakers, headphones, earphones, and alarms, and haptic output devices, including force-feedback game controllers and vibrating devices.

The processor 210 may be further coupled to a network interface 250, including a receiver 252 and a transmitter 254. The transmitter 254, in conjunction with the network interface 250, prepares data generated by the processor 210 for transmission over a communication network according to one or more network standards. The receiver 252, in conjunction with the network interface 250, demodulates data received over a communication network 125 according to one or more network standards. In one embodiment, the transmitter 254 and the receiver 252 are part of the same component, such as, for example, a transceiver. In other embodiments, the transmitter 254 and receiver 252 are two separate components.

One embodiment disclosed herein is a suite of web-accessible tools and services for the management of claims. Aspects include tools to facilitate the creation of more accurate PDE files, the calculation of financial data, the tracking and correction of PDE edits, and management of eligibility benefits. Each of these aspects, and others, are described below with respect to FIG. 3, FIG. 4, and FIG. 5.

PDE Generation and Error Tracking Tools

Figure 28:
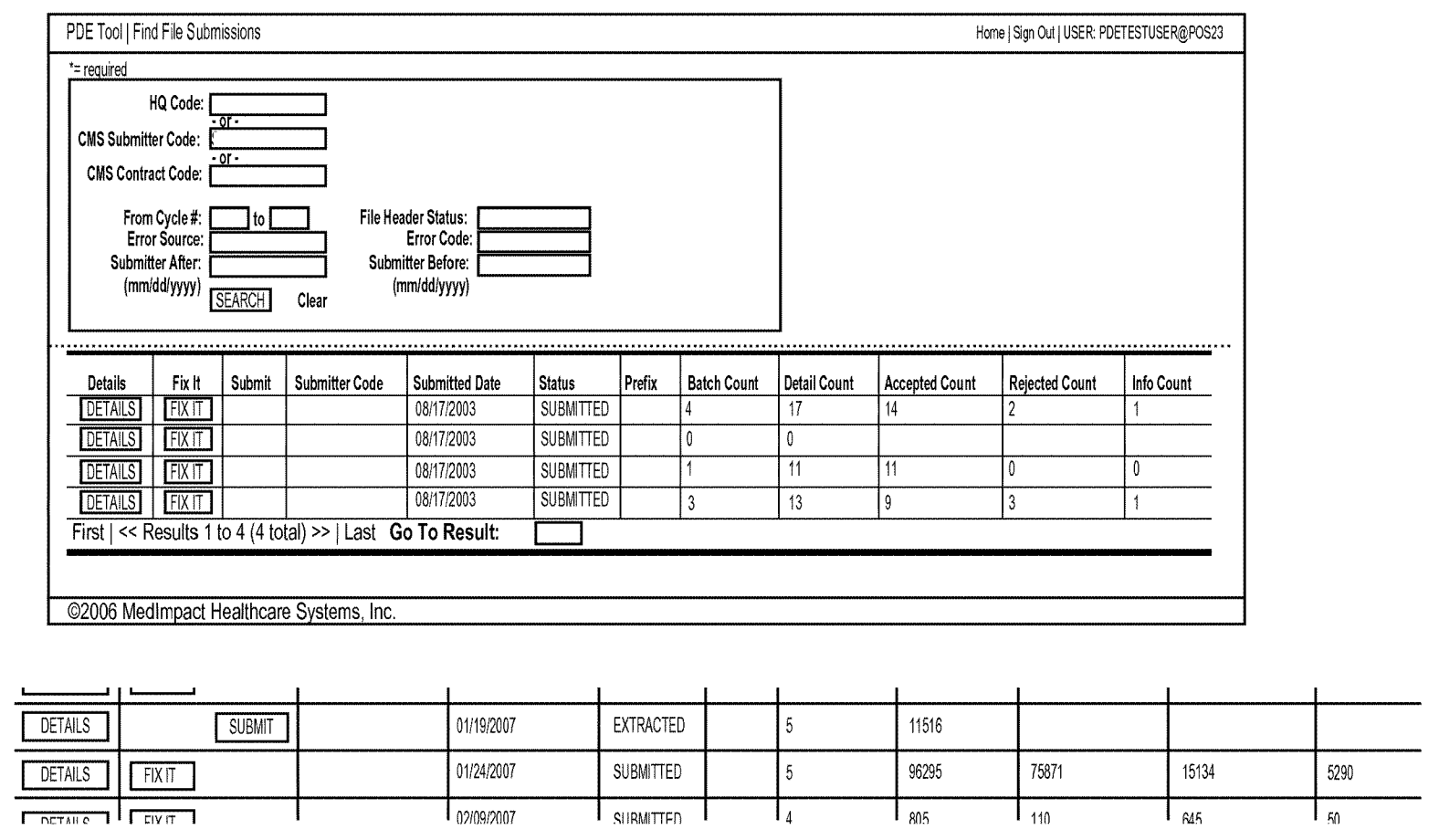

One aspect of the system is a tool for creating accurate PDE files based on claim information submitted by a user. The system can be configured to create and identify or track errors associated with PDE file generation and to correct certain errors with PDE files. The system can include one or more of the following non-limiting functionalities: (1) Creation of more accurate and up-to-date PDE files using the latest eligibility and claim information at the time of creating the files. (2) Research capability whereby data can be queried with specific search criteria for example as shown in FIGS. 28 and 32. For example, the user can search by claim, member, member number, family position, range of edits, PDE error code, Rx number, and/or date of service (for example as shown in FIGS. 35 and 36. (3) Interactivity that permits the system to be accessed via a web interface including different levels of access for different users based on a security level associated with each user. (4) Reports can be generated to allow maximal understanding and review of the complex data. The reports can provide information on the status of a member's benefit, plan or contract level reports, etc. Various types of reports may be generated including PDE Rejection reports which list the PDE rejections, PDE Rejection Detail reports, PDE Informational Detail reports, and PDE Summary Count (PDE submission log) reports. (5) The systems provides flexibility in quickly obtaining progressively more specific information in connection with PDE files (e.g., the ability to "drill down" more and more specifically.). (6) Permits historical data to be accessed for each PDE claim and track the outcome of record submission including, for example, member eligibility data at the time a claim was entered.

Figure 3:
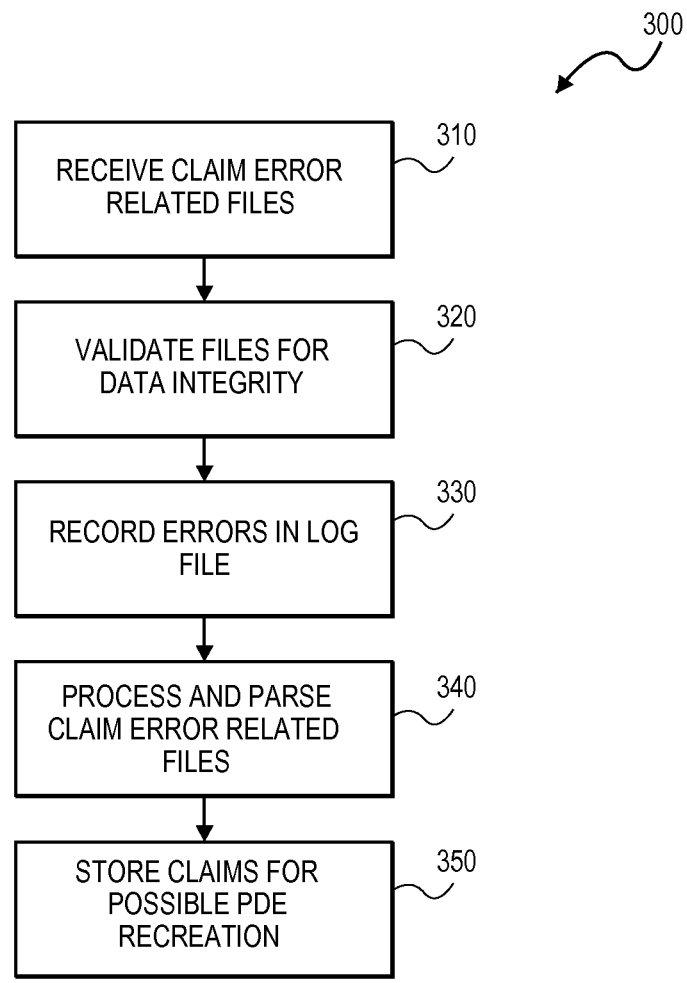
FIG. 3 is a flowchart illustrating an example of a method of loading and processing previously generated PDE claim files into the claim management system of FIG. 2

FIG. 3 is a flowchart which illustrates an example of a process 300 for loading and processing previously generated PDE files and errors into the claim management system 200 of FIG. 2. Such PDE files and errors may have been generated using a system other than the claims management system 200. The process 300 begins in block 310, in which claim error related files (e.g., DDPS files and/or comments or notes for a particular rejection or edit listed in a DDPS file) are received at the claims management system 200. The error related files can be received, for example, by the processor 210 of FIG. 2 via the network interface 250 and stored, for example, in the memory 220. The error related files may be received from a claims provider, for example. In one embodiment, the error related files are received via a web-based interface and stored in a web-accessible database.

After receiving the files, the process 300 continues to a block 320. In block 320, the system validates the DDPS file for data integrity, such as by verifying header/trailer counts, format, etc. In one embodiment, the processor 210 of FIG. 2 can perform this function based on software stored in the memory 220. In one embodiment, the processor 210 verifies there are only one File Header Record (HDR) and one File Trailer Record (TLR). The processor 210 further verifies the HDR is the first line of the DDPS file and the TLR is the last line of the file. The processor 210 also verifies there is at least one Batch Header (BHD) and one Batch Trailer (BTR). Further, the processor 210 verifies that the BHD comes before the BTR in the file and that they match a sequence number in the DDPS file.

Continuing, the processor 210 validates each line or record in the DDPS file. The processor 210 verifies the record type of each line is valid, for example, is one of HDR, TLR, BHD, BTR, or Detail Records (DET). The DET can have a value of ACC, REJ, or INF (e.g., accept, reject, informational). If the record type is one of the DET values, the processor 210 verifies whether the following six fields are populated: 1) Cardholder ID; 2) Date of Service; 3) Prescription Service Reference No.; 4) Product Service ID; 5) Service Provider ID; 6) Fill Number.

Further, the processor 210 validates the record counts in the DDPS file by: matching the count of detailed records in each batch with a DET RECORD TOTAL in the BTR; matching the total count of detailed records in file with the DET RECORD TOTAL; and/or matching the total count of batch records in the file with a BHD RECORD TOTAL in the BTR. The processor 210 also verifies each sequence number for each record appears only once in the DDPS file and verifies all contracts/plans listed in the incoming file are loaded in the system 200.

Next, in block 330, any error found during the validation process performed in block 320 is recorded in a log file which can be reviewed by an administrator of the system and/or the user. Further, in block 340, the validated DDPS files are processed and parsed, and claim information is stored in the memory 220. In one embodiment, the processor 210 cycles through each record in the DDPS file and inserts the records as data objects in the system 200. The processor 210 may not store DET information of the record if: the Date of Service is before a certain date (e.g., Jan. 1, 2009) and/or any of the six fields associated with a DET record are missing. For records that are after the date and have information for the six fields, the processor 210 further processes each record. For example, the processor 210 may map a control number associated with each record to a new claim identification number used by the system 200 for identification of the record. The processor 210 then checks whether any existing records have the same values for the six fields as a new record being entered from the DDPS file. If matching records are found, the same Claim ID is given to each record as they are duplicate records. Continuing at the step 350, the claims records may be stored along with other claim records in the system 200 as described herein.

Figure 4:
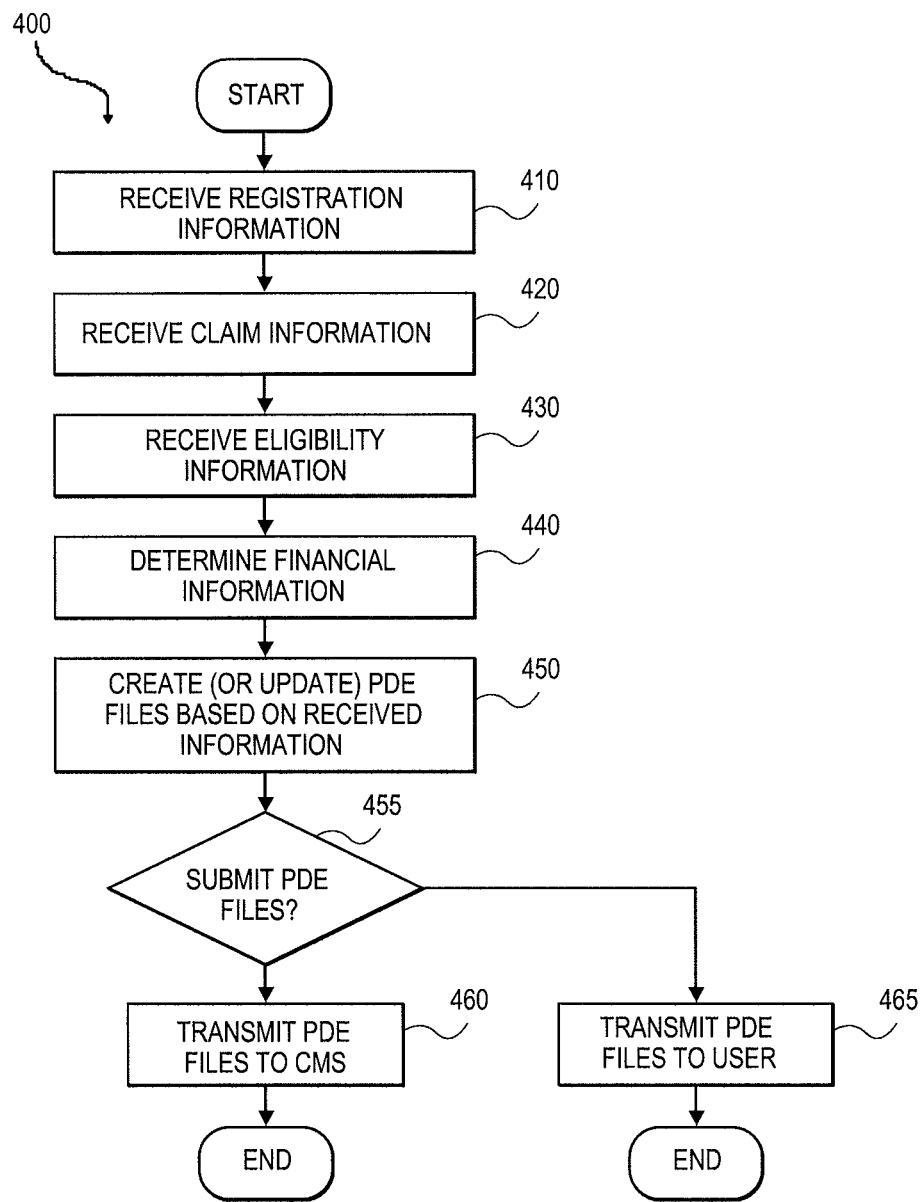
FIG. 4 is a flowchart illustrating an example of a method of generating PDE files.

FIG. 4 is a flowchart which illustrates an example of a process 400 of generating PDE files. The process 400 may be performed by the claims management system 200 of FIG. 2. In order to access the system, a user may first register with the system by providing certain information. Thus, the process 400 begins in block 410, in which registration information is received from a user. The registration information can be received, e.g., by the processor 210 of FIG. 2 via the network interface 250 and stored in the memory 220. In one embodiment, the registration information is received via a web-based interface and stored in a web-accessible database. The registration information can include, among other things, PDE Submitter IDs, CMS Contract IDs, and Plan Benefit Package (PBP) IDs along with the associated Part D plan type for each PBP ID. Part D plan types supported by the system include Defined Standard Benefit plans, Actuarial Equivalent plans, Basic Alternative plans, Enhanced Alternative plans, Flexible/Fixed Capitated plans, and Employer Group plans.

In one embodiment, the system certifies at least part of the registration information. For example, the system can ensure certification of the user's PDE Submitter ID by completing certain PDE certification tests. This facilitates the production of PDE files for the user in the correct format with correct data values prior to processing and submission of the PDE files by the system on behalf of the user.

CMS expects to receive PDE files from claimants on, at least, a monthly basis. Users of the system may want to submit PDE files to CMS more frequently. Thus, in one embodiment, the registration information can include submission scheduling information. The submission scheduling information may include PDE submission timing information or PDE submission frequency information. In one embodiment, the submission scheduling information indicates that PDE submissions are to occur monthly. In other embodiments, the submission scheduling information indicates the PDE submissions are to occur weekly, daily, or at irregular intervals.

As mentioned above, in one embodiment, the registration information is received via a web-based interface and stored in a web-accessible database. Storage in the web-accessible database may require a reformatting of the received information by the system. The web-based interface further allows the user to view and modify information in the database. For example, the user can access the web-based interface and revise the submission scheduling information to indicate that PDE files are to be submitted more or less frequently. As another example, the user can access the web-based interface and add a new PBP ID and associated Plan D type.

After registration, the process 400 continues to block 420 in which claim information is received. Like the registration information, the claim information can be received, e.g., by the processor 210 of FIG. 2 via the network interface 250 and stored in the memory 220. In one embodiment, the claim information is received via the web-based interface and is stored in the web-accessible database. The claim information can include original claims, claim reversals, and claim adjustments. In one embodiment, the claim information contains information regarding a number of claims for reimbursement for filled prescriptions, each claim containing information such as a claim control number uniquely identifying the claim, a cardholder ID identifying who the prescription was filled for, a national drug code (NDC) indicative of the prescription filed, and a date of service indicative of when the prescription was filled.

The claim information can also include certain financial information, such as how much the prescription cost to fill, how much of the cost was paid by the receiver of the prescription, how much of the cost was due to the ingredients, a dispensing fee, or sales tax, how much of the costs was paid by a third party, etc. Additional non-limiting examples of claim information fields are shown in Table 1 below. It is to be appreciated that the fields shown in Table 1 illustrates are examples, and are in no way limiting. The fields may be received from the user or determined based on information in the system.

TABLE 1

Example Claim Information Fields
PDE Detail Record Data Population Table

| PDE Data Element Name | Description | Captured at Claim Adjudication Time | Established or Reestablished at PDE Creation Time |
|---|---|---|---|
| Record ID | Set to "DET" | | ✓ |
| Sequence Number | Counter starting from 0000001 | | ✓ |
| Claim Control Number | The MedImpact claims processing Claim ID for the claim | ✓ | |
| HICN | The HIC number from the member's eligibility record | | ✓ |
| Cardholder ID | The Member ID Number for the member | ✓ | |
| Patient DOB | The member's date of birth from the member's eligibility record | | ✓ |
| Patient Gender | The member's gender (sex code) from the member's eligibility record | | ✓ |
| Date of Service | The prescription fill date for the claim | ✓ | |
| Paid Date | Optional data element which is only required for Fallback Plans. This data element will not be populated (set to blank) for MA-PD and PDP plans. | | ✓ |
| Prescription Service Reference No | The Rx Number for the claim | ✓ | |
| Product Service ID | The 11 digit NDC for the claim | ✓ | |
| Service Provider ID Qualifier | Set to '07' indicating an NCPDP assigned service provider (or '08' for State License) (In the future this will change to NPI—National Provider ID) | | ✓ |
| Service Provider ID | The NCPDP (or NABP) number assigned to the service provider (In the future this will change to the NPI—National Provider ID) | ✓ | |
| Fill Number | The refill number on the claim | ✓ | |
| Dispensing Status | Set to blank indicating not specified | | ✓ |
| Compound Code | The compound code on the claim | ✓ | |
| Dispense as Written (DAW) | The Dispensed as Written code on the claim | ✓ | |
| Quantity Dispensed | The quantity dispensed on the claim | ✓ | |
| Days Supply | The days supply on the claim | ✓ | |
| Prescriber ID Qualifier | The Prescriber ID qualifier on the claim, typically set to "12" indicating a DEA assigned ID prescriber number (In the future this will change to NPI—National Provider ID) | | ✓ |

TABLE 1-continued

Example Claim Information Fields
PDE Detail Record Data Population Table

| PDE Data Element Name | Description | Captured at Claim Adjudication Time | Established or Reestablished at PDE Creation Time |
|---|---|---|---|
| Prescriber ID Number | The Prescriber ID the claim (In the future this will change to NPI—National Provider ID) | ✓ | |
| Drug Coverage Status Code | Set during adjudication time to appropriate value of: "C"—Covered Part D drug "E"—Enhanced drug "O"—Over-the-counter drug | ✓ | |
| Adjustment/Deletion Code | Set during PDE creation with value of: blank—Original PDE "A"—Adjust PDE "D"—Delete PDE | | ✓ |
| Non-Standard Format Code | Set during PDE creation with value of: blank—NCPDP standard format "X"—X12-837 claim format "B"—Beneficiary DMR claim "P"—Provider paper claim | | ✓ |
| Pricing Exception Code | Set during PDE creation with value of: blank "O"—Out of Network "M"—Medicare as Secondary Payer | | ✓ |
| Catastrophic Coverage Code | Set during PDE creation with the value of: blank—claim is below attachment point "A"—claim is at attachment point "C"—claim is above attachment point | | ✓ |
| Ingredient Cost Paid | Ingredient cost paid to the service provider | ✓ | |
| Dispensing Fee Paid | Dispensing fee paid to the service provider | ✓ | |
| Amount Attributed to Sales Tax | The dollar amount of sales tax for the claim | ✓ | |
| Gross Drug Cost Below Out of Pocket Threshold (GDCB) | The ingredient cost paid + dispensing fee paid + amount attributed to sales tax for claims below the attachment point | | ✓ |
| Gross Drug Cost Above Out of Pocket Threshold (GDCA) | The ingredient cost paid + dispensing fee paid + amount attributed to sales tax for claims above the attachment point | | ✓ |
| Patient Pay Amount | The amount paid by the beneficiary | | ✓ |
| Other TrOOP Amount | Amounts paid by TrOOP-eligible parties other than the patient and amounts attributed to LICS | | ✓ |
| Low Income Cost-Sharing Subsidy (LICS) | The dollar amount attributed to LICS | | ✓ |
| Patient Liability Reduction Due to Other Payer Amount (PLRO) | Amounts paid by entities to reduce patient costs that do not count as TrOOP | | ✓ |
| Covered D Plan Paid Amount (CPP) | The net amount the plan paid for "C" covered Part D drugs | | ✓ |
| Non-Covered Plan Paid Amount (NPP) | The net amount the plan paid beyond the standard/basic benefit | | ✓ |
| Estimated Rebate at POS | Rebate amount captured at time of adjudication | N/A | N/A |

TABLE 1-continued

Example Claim Information Fields
PDE Detail Record Data Population Table

| PDE Data Element Name | Description | Captured at Claim Adjudication Time | Established or Reestablished at PDE Creation Time |
|---|---|---|---|
| Vaccine Administration Fee | The amount associated to the administration cost of a Vaccine claim | ✓ | |
| Rx Origin Code | Prescription Origin code values are:<br>'0' = Not Specified<br>'1' = Written<br>'2' = Telephone<br>'3' = Electronic<br>'4' = Facsimile | ✓ | |

In one embodiment, the claim information may include claim adjustment information. The claim adjustment information can include for example retroactive LICS adjustments, adjustments as a result of Medicare Part D member true up activity, adjustments resulting from coordination of benefits, and other claim level adjustments. The claim adjustment information may be used to generate an adjusted PDE record as described below.

In one embodiment, receiving the claim information in block 420 may include a validation process. The validation process may result in rejections by the system of the claim information or specific claim records of the claim information. The rejections may be based, for example, upon an invalid contract/plan combination for that health plan, a PDE file having payment fields which do not add up to cost fields, or any missing or invalid data elements. In one embodiment, validation results are captured on a load report and all rejected records are written to a rejected claim file for further research and correction. In one embodiment, the errors are automatically corrected by the system. In another embodiment, the errors are manually corrected by a system administrator. In yet another embodiment, the errors are returned to the user for correction. After the errors have been corrected, the system receives corrected claim information and can incorporate the corrected claim information into the process 400. In another embodiment, the process 400 continues using only the validated records.

The claim information can be received in a number of file formats, including as a spreadsheet or a database file. The claim information can be received as a plurality of data objects, each object corresponding to a single claim and associated with a number of data fields. In one embodiment, additional data fields can be added to the claim information by the system, including a status field and a comment field.

As mentioned above, in one embodiment, the claim information is received via the web-based interface and is stored in the web-accessible database. Storage in the web-accessible database may require a reformatting of the received information by the system. The web-based interface further allows the user to view and modify information in the database. For example, based on a PDE edit received from CMS, the user can access the web-based interface and revise the date of service to correct a typographical error. As another example, the user can access the web-based interface and determine the status of a particular claim or set of claims or add comments regarding the claim into the comments field.

Next, in block 430, eligibility information is received. Although blocks 420 and 430 are described sequentially, it is to be appreciated that the actions represented by the two blocks may be performed simultaneously, overlapping in time, or in reverse order. Like the claim information, the eligibility information can be received, e.g., by the processor 210 of FIG. 2 via the network interface 250 and stored in the memory 220. In one embodiment, the eligibility information is received via the web-based interface. The eligibility information provides information about the plan members for whom prescriptions were filled. The eligibility information includes an identifier, such as a Health Insurance Claim Number (HICN), identifying the member for whom the prescription was filled. The HICN is a number assigned by the Social Security Administration (SSA) to an individual identifying him or her as a Medicare beneficiary. The eligibility information can further include a cardholder ID, effective dates of plan membership, a CMS Contract ID, a PBP, or a gender of the member. Other information, including member name, date of birth, and LISC level can also be included.

As with the claim information described with respect to block 420, the eligibility information can be received in a number of file formats, including as a spreadsheet or a database file. The eligibility information can be received as a plurality of data objects, each object corresponding to a single member and associated with a number of data fields.

In one embodiment, receiving the eligibility information in block 430 may include a validation process. The validation process may result in rejections by the system of the eligibility information or specific members of the eligibility information. The rejections may be based, for example, upon an invalid format for member records or a lack of data integrity. In one embodiment, validation results are captured on a load report and all rejected records are written to a rejected eligibility file for further research and correction. In one embodiment, the errors are automatically corrected by the system. In another embodiment, the errors are manually corrected by a system administrator. In yet another embodiment, the errors are returned to the user for correction. After the errors have been corrected by the user, the system receives corrected eligibility information and can incorporate the corrected eligibility information into the process 400. In another embodiment, the process 400 continues using only the validated records.

Eligibility information can be submitted by the user as often as desired, for example, once a day. As eligibility information is received or updated, the most recent information is used in the generation of PDE files as described below with respect to block 450. It is to be appreciated by those of skill in the art that more up-to-date eligibility information available to system results in more accurate PDE data submissions.

As mentioned above, in one embodiment, the eligibility information is received via the web-based interface and is stored in the web-accessible database. Storage in the web-accessible database may require a reformatting of the received information by the system. The web-based interface further allows the user to view and modify information in the database. For example, based on a PDE edit received from CMS, the user can access the web-based interface and revise the eligibility information to indicate a correct LICS level or a retroactive date of eligibility. As another example, the user can access the web-based interface and determine the current eligibility status of a particular member or set of members. Further, a user can access the web-based interface and determine the eligibility status of a particular member associated with a particular claim as it was on the date of service of the particular claim. Advantageously, this aids a user to determine whether a claim was denied due to the member lacking eligibility at the time a claim was serviced.

At block 440 the system determines financial information. For example, this can be done using the information received in block 420 and 430. In one embodiment, the processor 210 of FIG. 2 determines the financial information based on software stored in the memory 220. Periodically, the system may review and update claim information and/or eligibility information to accurately update the current year-to-date True Out of Pocket (TrOOP) and year-to-date gross covered drug costs for each beneficiary and the claim information associated with the beneficiary. TrOOP can be important because, after spending a certain amount of money out-of-pocket, the beneficiary is eligible for Catastrophic Coverage.

The system can update these, and potentially other, amounts when Part D claims have been reversed or adjusted. The current or recalculated year-to-date TrOOP and year-to-date gross covered drug costs for each claim can be used by the system in the calculation and creation of PDE adjustment records when certain financial PDE file data elements change as a result of changes to the year-to-date TrOOP and year-to-date gross covered drug costs for an original or adjusted PDE. Financial PDE file data elements include Gross Drug Costs Below Out of Pocket Threshold (GDCB), Gross Drug Costs Above Out of Pocket Threshold (GDCA), Covered Part D Plan Paid Amount (CPP), Non-Covered Plan Paid Amount (NNP), and a Catastrophic Coverage Code. In one embodiment, the system reviews and updates all claim information daily based on the determined financial information. In one embodiment, the calculation of PDE adjustment records is based on calculation logic (e.g., equations) stored in configuration tables. The system may support multiple configuration tables, such that a user and/or an administrator such as a claims processor may choose which configuration table to use for calculations. For example, a default configuration table may typically be used. A user can instead use a custom configuration table with custom calculation logic to replace the default configuration table. In one embodiment, the calculation logic may be substituted or updated via the web interface.

PDE files can be created or updated, in block 450, based on various claim events, enrollment events, claim adjustment events, and PDE correction events, using the information received and determined in the previous step or steps of the process 400. In one embodiment, the PDE files are created by the processor 210 of FIG. 2 based on software stored in the memory 220.

A large number of events can trigger the creation or updating of PDE files. Therefore, it will be appreciated that a system, such as the claim management system 200 of FIG. 2, which automates or at least facilitates the generation of PDE files likely to be approved by CMS, thereby increasing the revenue of the user, is desirable. Examples of claim events which can trigger creation or updating of a PDE file include newly adjudicated original Part D claims and Part D claim reversals. Examples of enrollment events which can trigger creation or updating of a PDE file include retroactive termination of a member's eligibility within the Part D plan, such as when a member switches to another Part D plan. Examples of claim adjustment events which can trigger creation or updating of a PDE file include a retroactive change in LISC status or institutionalized status of a member, claim reversals or adjustments for a member that change the current year-to-date True Out of Pocket (TrOOP) or year-to-date gross covered drug costs on other claims with a member's experience, claim adjustments required to properly move claims from one level of the Part D benefit to another due to retroactive changes that impact TrOOP payments, secondary claim processed by another health insurance, mistaken payment amounts recovered from other insurers that are found to be in a primary position compared to Medicare, retroactive application of a member's Part D TrOOP and gross covered drug costs when a member switches Part D plans, and any other claim adjustment that adjusts the member, plan, pharmacy, or other payer payments on a Part D claim. Examples of PDE correction events which can trigger creation or updating a PDE file include resubmission of claim information for claims which have been rejected by CMS or removal of claims that the user indicates should be excluded from PDE reporting. In another embodiment, a user can initiate the creation or updated of PDE files, such as through the web interface, for example as shown in FIGS. 24-27. In another embodiment, a user can query and manage the PDE file generation process, such as through the web interface, for example, as shown in FIGS. 24-27.

The system can create and update PDE files to include the appropriate header, batch headers, detail records, batch trailers, and file trailer records. The system also can ensure that the PDE files are in the appropriate sort order and file format. In one embodiment, the PDE files are generated based on specifications outlined by CMS in PDE guidance and training materials.

The system creates and formats the appropriate file header and batch headers for each PBP and Contract ID for the PDE reporting period. Many of the data elements of the PDE file are determined during claim adjudication by the user and are included in the received data. Other of the data elements in the PDE file are determined or calculated by the system as part of the PDE file generation process. For example, the received data can include the amount paid to the service provider (e.g., pharmacy) for a prescription by the user and by the beneficiary. From this and other information, such as the eligibility information of the beneficiary, the system can determine the Covered D Plan Paid Amount (CPP) and Non-Covered Paid Plan Amount (NPP). This allows for the most up-to-date information to be reported to CMS, taking into account such events as subsequent claim reversals or claim adjustment activity that may have occurred.

In one embodiment, creating (or updating) the PDE files in block 450 may include a validation process. In one embodiment, the validation process is performed by the processor 210 in FIG. 2 based on software stored in the memory 220. The validation process may substantially minor that performed by CMS, thereby reducing PDE edits. The validation process may result in rejections of the PDE file or specific records of the PDE file. In one embodiment, invalid records are marked for correction and valid records are extracted into a validated PDE file in the required batch and sort order.

In one embodiment, the invalid records are automatically corrected by the system. In another embodiment, the errors are manually corrected by a system administrator. In yet another embodiment, the errors are returned to the user for correction. After the errors have been corrected, the system receives corrected information.

In one embodiment, creating (or updating) the PDE files in block 450 can include a reporting process in which a PDE File Submission Log Report is generated for review by a system administrator or the user. The PDE File Submission Log Report can be stored in the memory 220 of FIG. 2 or transmitted to the user via the network interface 250. In one embodiment, the PDE File Submission Log is stored in the web-accessible database for access by the user via the web-based interface. The system administrator or the user can perform additional quality checks before submission of the PDE file to CMS.

In one embodiment, after creating the PDE file in block 450, but before submission of the PDE file to CMS and before a DDPS response file is received, the claims management system 200 allows a user to void a cycle that contains the PDE file data that is to be submitted to CMS. For example, the user may determine there is an error with the data of the PDE file, and therefore not want to submit the PDE file. Accordingly, the cycle can be voided and the PDE file recreated before submission to CMS.

After creating the PDE files, the process moves to decision block 455, where it is determined if the user has requested that the PDE files be submitted to CMS on the user's behalf. This determination may be based on the registration information received in block 410. If it is determined that the user has not requested that the PDE files be submitted to CMS on the user's behalf, the process 400 moves to block 465 in which the PDE files are transmitted to the user. The PDE files can be transmitted, for example, via the network interface 250 of FIG. 2. In one non-limiting embodiment, the user retrieves the PDE files via the web-based interface.

If it is determined that user has requested that the PDE files be submitted to CMS on the user's behalf, the process 400 moves to block 460 in which the PDE files are transmitted to CMS. The PDE files can be transmitted via the network interface 250 of FIG. 2 or via a separate CMS interface. In one embodiment, the claims management system 200 allows a user to skip one or more claims in the PDE file and submit less than all of the claims to CMS. Once the PDE files have been transmitted, CMS performs an initial review of the file and either accepts or rejects the file. Rejected files are returned by CMS to the system. In one embodiment, the system automatically loads and updates the record and then resubmits rejected records. In another embodiment, a system administrator corrects the files and the system resubmits them. In yet another embodiment, a user can view the rejected files and review member data for any rejected claims as the member data was on the date of the claim. The user may use such information to correct files, such as reversing claims for which the member did not have eligibility.

Accepted files are moved, by CMS, to the Drug Data Processing System (DDPS). The DDPS reviews the PDE file on an individual record level and each record is determined to be accepted, have an informational edit, or be rejected by CMS. Claimants are reimbursed for claims which are accepted and for claims which have been subjected to an information edit. Claimants are not reimbursed for claims which are rejected; however, the claimant is provided a limited time (12-18 months) to correct and resubmit the rejected claim. Like an original claim, a resubmitted claim can be accepted, have an informational edit, or be rejected.

The unique systems and methods described above have resulted in surprisingly drastic reductions in PDE file error rates upon submission to CMS. The reduction in errors means fewer resources must be expended to correct the errors and results in more rapid and complete reimbursement of Medicare Part D claims.

PDE WorkFlow Management

While it is certainly desirable to submit error-free PDE files, PDE errors can occur for a variety of unpredictable reasons. From the perspective of the user, PDE edits represent lost revenue from CMS. When PDE file edits are reported in a DDPS file they are not presented in a format that enables a user to quickly identify PDE edits by edit type or by the age of the edit. This is further complicated by the fact that a single claim may have more than one error. As a result, many edits are simply re-submitted to CMS without ever being reviewed, and continue to be rejected in subsequent cycles.

Embodiments described herein permit a user to view or access PDE file edits in a more organized and useful manner such that the user can quickly pinpoint certain PDE edits by edit type. This gives the operator the ability to find certain edits that either occur frequently or have more severe financial repercussions for the plan sponsor when they do occur. In addition, some embodiments permit the user to view or access PDE edits by edit age. This gives the operator the ability to quickly pinpoint edits that had not been resolved for long periods of time, and to identify recurring edits, and thus prevent edits from simply being re-submitted without review to (and rejected by) CMS.

Further, some embodiments permit the PDE edits to be organized or viewed together with comments written by the system user(s). In such a system, the computer user can input and store annotations together with the PDE edits. Such annotations may be used to explain how the edit is to be resolved, or to assign responsibility to the person or persons responsible for correcting the edit. The system can be configured such that the comments and or other review status identifiers can be used automatically route particular claims to an appropriate entity for correction, for example, to a department that specializes in a particular type of edit/error.

Also, comments or notes from one cycle to another can be maintained so that the system can display a cumulative or rolling history of such comments or notes. For example, if a particular claim is rejected with edit code 705 in a first cycle, the user can enter comments/notations regarding this error. If the same claim is rejected with edit code 705 in a second cycle, the user can see the comments/notations from the first cycle and can add additional notes or comments. This allows a user to view a cumulative history of the rejections, comments made, and actions taken regarding the particular claim. The cumulative history of comments can be maintained, for example, until the claim and/or error code edit is resolved.

Existing PDE file edit reporting systems are typically not easily searchable. As a result, a significant amount of time is spent combing through charts of data when attempting to locate and correct edits. Such time would instead be much better spent on resolving the PDE edits (such that the PDE files could be quickly re-submitted to CMS for approval). The systems described herein permit searching.

Also, there is typically often a long time delay between when the PDE edit is first found and when it is reported to the user in a format the user can use to begin working on correcting the edit. Some embodiments relate to systems that are accessible via a web-interface for example, and which permit real-time reporting and accessing of information.

Therefore, another aspect of the system advantageously provides tools for simplifying the tracking and correction of errors. The tools can include, for example, the following non-limiting functionalities: (1) An aging tool that is configured to assist the user in organizing error correction workload of PDE edits based upon the age of the edit and/or the priority of correcting a particular edit. (2) A tracking tool to quickly identify and mark errors that have already been handled, which can help avoid wasting resources on correcting errors for which no further action is currently required. (3) A priority tool configured to identify "high" priority errors, for example with business-defined rules. For example, some claims may not ever be reimbursable due to the eligibility status of the user. It may be important to assign a higher priority to catching such errors quickly to avoid the continued submission of such claims. (4) A detection tool configured to identify error trends and work on root cause analysis. (5) An assignment tool configured to route errors to the appropriate person, entity or department, for example, a department with particular expertise or responsibility for the type of error. (6) A metric tool configured, for example, to identify turn-around time metrics to track resolution progress by error type.

Figure 5:
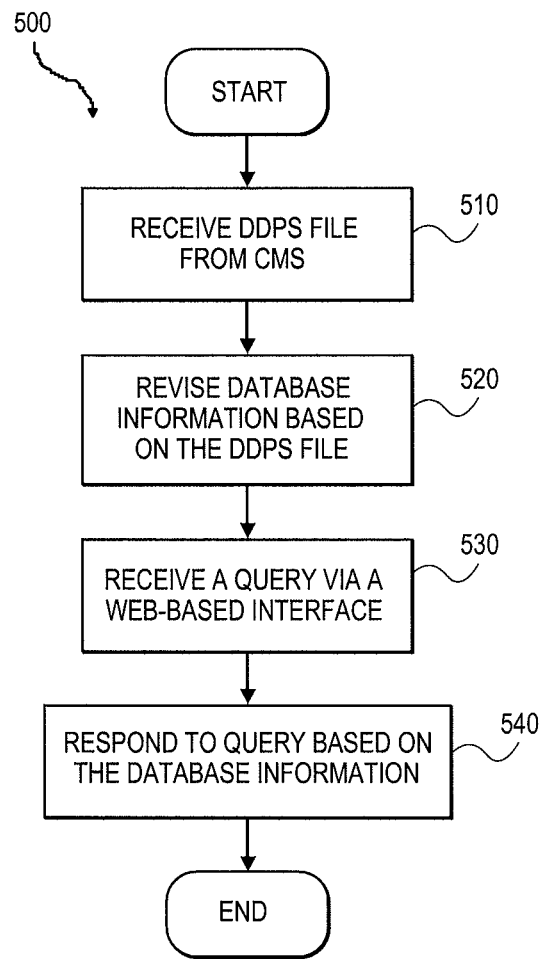
FIG. 5 is a flowchart illustrating an example of a method of managing claims.

FIG. 5 is a flowchart illustrating an example of a method 400 of managing claims.

The process 400 begins, in block 510 with the reception of a DDPS transaction validation response file (a "DDPS file") containing information such as which records are accepted, accepted with an information edit, or rejected. The edit code associated with each edited or rejected record is also included in the DDPS file. The DDPS file can be received, for example, by the processor 210 of FIG. 2 via the network interface 250 or via a separate CMS interface.

Next, in block 520, the system parses the DDPS file to generate updates to claim objects stored in the database and revises the claim object information based on the information in the DDPS file. In one embodiment, the processor 210 of FIG. 2 can revise the claim information stored in the memory 220. The processor 210 can perform this function based on software stored in the memory 220. As mentioned above with respect to FIG. 4, in one embodiment, the claim information can be stored as a plurality of data objects in a web-accessible database, each object corresponding to a single claim and including a number of data fields. The data fields can include a current status field, a history field, and a comment field.

It should be noted that as part of block 520, the system also can receive comments or notes for a particular rejection or edit listed in a DDPS file. For example the comments or notes from one cycle to another can be maintained so that the system can display a cumulative or rolling history of such comments or notes. For example, if a particular claim is rejected with edit code 705 in a first cycle, the user can enter comments/notations regarding this error. If the same claim is rejected with edit code 705 in a second cycle, the user can see the comments/notations from the first cycle and can add additional notes or comments. This allows a user to view a cumulative history of the rejections, comments made, and actions taken regarding the particular claim. The cumulative history of comments can be maintained, for example, until the claim and/or error code edit is resolved.

In one embodiment, a processor such as, for example, the processor 210, parses the DDPS into a plurality of claim object update data such that each claim object update data is associated with a single claim object and contains information received from DDPS about the claim associated with the claim object. The claim object update data can include, for example, an edit code to be added to the associated claim object, or the edit code and the date the edit code was received from CMS.

As an example of claim information being revised by the system based on the information in the DDPS file, if the DDPS file indicates that a specific claim number was rejected with edit code 705, the system may revise the claim information associated with that claim by adding additional information to indicate that the claim was so edited.

If the error is not resolved prior to the next submission, it is expected that the DDPS will again indicate that the claim was edited for the same reason. The system can again revise the claim information corresponding to the claim indicating that the claim was edited again. For example, edits and comments can be received or noted by the system, and the comments or notes from one cycle to another can be maintained so that the system can display a cumulative or rolling history of such comments or notes. In this way, the claim information may contain a cumulative history of the claim in addition to the current status. The history of the claim can also include information regarding when the claim was first received, when claim was submitted to CMS, when the claim information was revised by the user and the nature of the revision, or when the claim was edited and the nature of the edit. In reviewing the claim history via a web-based interface, the user can more efficiently determine the nature of an error and correct it.

For example, a user may access the claim information in the web-accessible database via a web-based interface for a particular claim and notice that it has been edited with edit code 608 (indicating that the date of service is not on/after Jan. 1, 2006). In response, the user checks the date of service field of the claim information and notices that it has been entered as Dec. 13, 1908, an obvious typographical error. Perhaps after confirming the data with the user's internal records, the user revises the date of service to Dec. 13, 2008. During the next submission cycle, assuming no other edits are applicable to the claim, the claim will be accepted by CMS.

This revision is also stored in the claim information. Additionally or alternatively, a comment or additional notes may be added by the user indicating that this claim has been revised and what was done to revise it. Thus, if another user accesses the claim information before or after resubmission to CMS and notices that it has been edited with edit code 608, the claim history fields or the comment fields will indicate that no further action is needed.

In block 530, a query is received via a web-based interface. In one embodiment, the user submits a query to the web-accessible database. The query may be submitted via a search page of the web-based interface (such as that shown in FIG. 7) or may be a request for a particular report (such as those shown in FIG. 10 and FIG. 11). In response to receiving a query, the system, in block 540, responds to the query based on the information in the database.

In one embodiment, the query is received via the network interface 250 of FIG. 2 and processed by the processor 210 to generate response data. This processing involves searching a database within the memory 220 for records that match the query. The response data is then transmitted via the network interface 250.

A number of different queries are supported by the system. In one embodiment, the query can request information regarding a particular claim. In response, the system presents, via the web-based interface, the claim information stored in the database. In another embodiment, the query can request information regarding a particular member. In response, the system presents, via the web-based interface, the eligibility information stored in the database.

In one embodiment, the query may request information regarding the set of claims meeting specific criteria. In response, the system searches the database and presents the claim information meeting the specific criteria. The query can request information regarding the set of claims edited with a specific edit code, claims which have been pending and not accepted for a certain period of time, or claims which have a date of service within a particular date range. In response to the query, the system may present only subset of the information. For example, if a user submits a query requesting information regarding claims edited with a specific edit code, the system may return a list of claim numbers associated with claims edited with the specific edit code. The user can request additional information (submit an additional query) by clicking one of the claim numbers via the web-based interface. In using the web-based interface, the user can "drill down" through the data to see, for example, all current edits, search for current edits with edit code 705, limit the search to current edits with edit code 705 which have been pending for more than six months, and finally view a specific claim in order to correct the error.

The submitted query can also be a request for a predefined report. In one embodiment, the system allows users to custom design and save a query as predefined report. This allows the user to prioritize errors for correction. One embodiment of a predefined report is a PDE Rejection Summary Report which summarizes the rejected records by PBP and reports the number of affected beneficiaries. Another embodiment of a predefined report is a PDE Rejection Detail Report which provides claim level detail for each rejected PDE edit. This report provides information on the total number of records as well as the total number of beneficiaries affected. Another embodiment of a predefined report is a Year-To-Date Rejection Summary Report which summarizes, by month, the number of records that have been rejected for each edit. This report assists users in monitoring their efforts, over time, to correct errors.

While the above processes 300, 400, and 500 are described in the detailed description as including certain blocks/steps and are described in a particular order, it should be recognized that these processes may include additional steps or may omit some of the steps described. Further, each of the steps of the processes does not necessarily need to be performed in the order it is described.

Example of a Web-Based Interface

One embodiment disclosed herein is a suite of web-accessible tools and services for the management of claims. One aspect of the system is a web-based interface for the tracking and correction of rejected claims. A particular embodiment of the web-based interface is described below and illustrated in FIGS. 6-11.

Upon directing a suitable web browser to the Uniform Resource Locator (URL) of the web-based interface, the user is presented with a login screen. The login screen includes fields for entering a user ID and a password. Upon entering a matching user ID and password and clicking a "SIGN IN" link, the user is directed to a main menu screen, also referred to as the home screen or dashboard.

FIG. 6 is a screenshot of an example of a dashboard screen. The bulk of the screen is occupied by an interactive table 610 detailing the number of records rejected per PDE edit code per cycle. The cycle numbers along the top of the table (e.g., 30, 31, 32, 33, 34, etc.) represent the original Medicare Part D claim cycle that the PDE errors first appeared in. These cycles were first started by CMS in 2006. One advantage of displaying the PDE edits by cycle is that edits which have not been corrected for some time, so-called aged edits, can be quickly identified. This is particularly important for users because, as noted above, claimants have a limited time to resubmit edited claims for reimbursement.

The table 610 also displays the total number of records rejected per PDE edit code. For example, the user can quickly determine that there have been 1104 instances of edit code 705 (beneficiary not enrolled) occurring, but only 11 instances of edit code 631 (Dispensing Fee Paid field is in error) occurring. This allows the user to spot trends and pinpoint commonly recurring edit codes such that additional efforts or strategies can be directed to resolving these edits.

In another embodiment, the presented table aggregates related PDE edit codes into edit code groups. For example, instead of each row representing a separate PDE edit, there may be a number of rows representing eligibility/enrollment edits, LICS edits, data entry edits, CMS internal edits, etc.

The table 610 can be sorted at least by edit code or total. Upon clicking a particular cell (e.g., cell 611) of the table, the user is redirected to a page showing the results of a search of claim records matching the edit code and cycle indicated by the row and column of the cell 611.

The screen also contains a toolbar 620 of hyperlinks which, when clicked, directed the user to other pages. The toolbar 620 can include links to, for example, the "dashboard" 621, a search page 622, a reports page 623, a FAQ page 624, and a sign-out page 629. Though not shown, the toolbar 620 may also include links to an import page. For consistency and ease of use, the toolbar 620 can be included on multiple pages of the interface. Those of ordinary skill in the art will recognize that more or fewer hyperlinks may be included on the toolbar 620 or elsewhere on the page. Further, as discussed above, different users may have different security levels. Accordingly, the information presented on the screen to the user may be dependent on the security level of the user.

As mentioned above, the dashboard contains a hyperlink to a search page 622. FIG. 7 is a screenshot of an example of a search page screen. The search page includes a search area 710 for the user to input search criteria and a results area 720 for the user to view results of the search. Both the search area 710 and the results area 720 are collapsible and expandable to allow the user to more efficiently use the screen space.

As mentioned above with respect to FIG. 4, the search criteria can include a variety of different fields. In response to the user clicking the "SEARCH" button 711, a query based on information input into these fields is submitted. In one embodiment, upon the user clicking certain of the input fields, a drop-down menu is presented showing the available search criteria. For example, upon the user clicking the CMS Contract field 712, the user may be presented with the CMS Contract IDs previously associated with the user. Such information may be provided as part of the registration information described above with respect to block 410 of FIG. 4. As another example, upon clicking the PDE Edit Code field 713, the user is presented with a drop-down menu listing the currently used edit codes. The drop-down menu may be sorted based on predefined priority rules or recent search history. The drop-down menu can also indicate the meaning of the available PDE edit codes. In another embodiment, the search page also can include a PDE Edit Code Group field, which upon being clicked, presents the user with a list of PDE edit code groups, such as those described above with respect to FIG. 6. Upon selection of one of these groups, the user can further narrow the search by selecting a PDE edit code from the group in a drop-down menu of the PDE Edit Code field 713. The search area 710 also includes a "VIEW ALL" button 715 for viewing all PDE edits.

In response to the user clicking the "SEARCH" button 711 or the "VIEW ALL" button 715, the search executes a search and provides the search results, which displayed in the results area 720. The results area 720 displays information about the claim records matching the criteria of the search. In one embodiment, only the claim number is displayed. In the embodiment illustrated in FIG. 7, the submission status, review status, claim number, date of service, PDE edit code, cardholder ID, CMS contract ID, CMS plan ID, last update, original cycle, current cycle, LICS level on date of service, and current LICS level are displayed. Others can be included if desired. In one embodiment, the information displayed in the results area 720 is customizable by the user.

The search area 720 also includes an "EXPORT" button 722, which, when clicked, prompts the system to generate and submit the results in a downloadable file format, such as CSV.

In response to the user clicking on one of the results or one of the "VIEW" buttons 721 proximal to each result, the user is directed to a record page with additional information regarding the specific claim record. FIG. 8 is a screenshot of an example of a record page. The record page includes a data area 810 and a comment area 820. The data area 810 displays information regarding a specific claim record. In one embodiment, the data area 810 can be revised by the user. The revision may be automatically recorded and displayed in a history area (not shown) or noted by the addition of a comment by the user in the comment area 820. The comment area can be used to add comments such as statements assigning responsibility to resolve the edits to certain persons or the strategy to be used in resolving the edit. The comment area 820 also displays comments previously entered. In one embodiment, the user is presented with a "quick comment" option which presents a list of text strings for selection either pre-defined by the system or the user.

Further, as mentioned above, the dashboard may contains a hyperlink to an import page. The import page, can include links and logic to allow a user to import comments and status for claim records from an external document.

Figure 9:
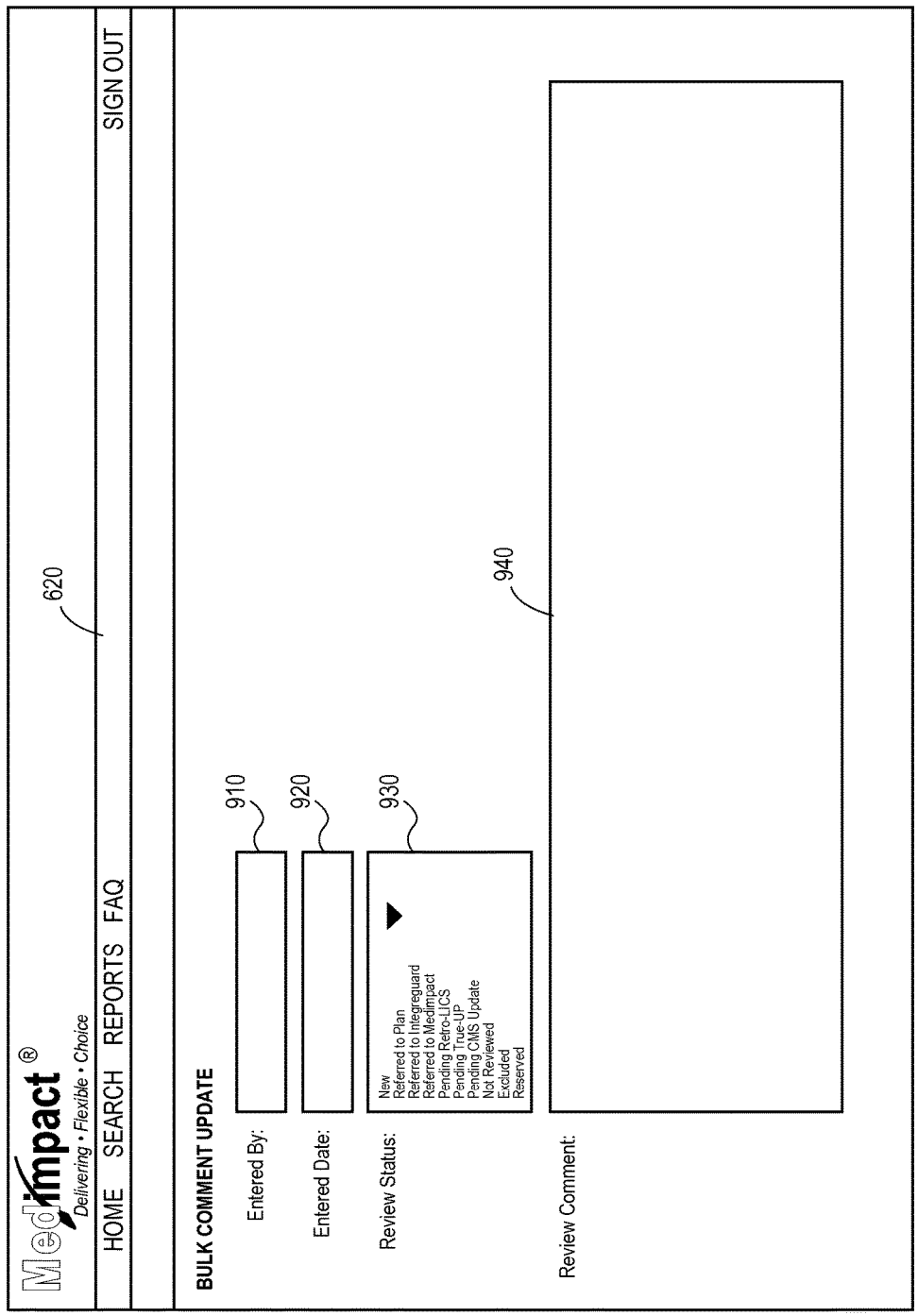
FIG. 9 is a screenshot of an example of a bulk update page.
Figure 12:
FIG. 12 is a screenshot of an example of a login screen.

Returning once again to FIG. 7, the results area 720 includes a "BULK UPDATE" button 723. By clicking on the "BULK UPDATE" button 723, the user is directed to a bulk update page for revising all of the selected records at once. FIG. 9 is a screenshot of an example of a bulk comment update page. The bulk update page includes an "Entered By" field 910 and an "Entered Date" field 920 which can be auto-populated based on the login information and the current date. The bulk update page also includes a "Review Status" field 930 which presents a drop-down menu for changing the review status of the records selected on the search page. In one embodiment, the drop-down menu is customizable by the user. The drop down menu also can be configured so that the selected option will trigger the system to route the record to a particular person, entity or department for correction of the error by the most appropriate person. The user can enter a comment in the comment field 940, which will be added to the claim information of the records selected on the search page.

Figure 10:
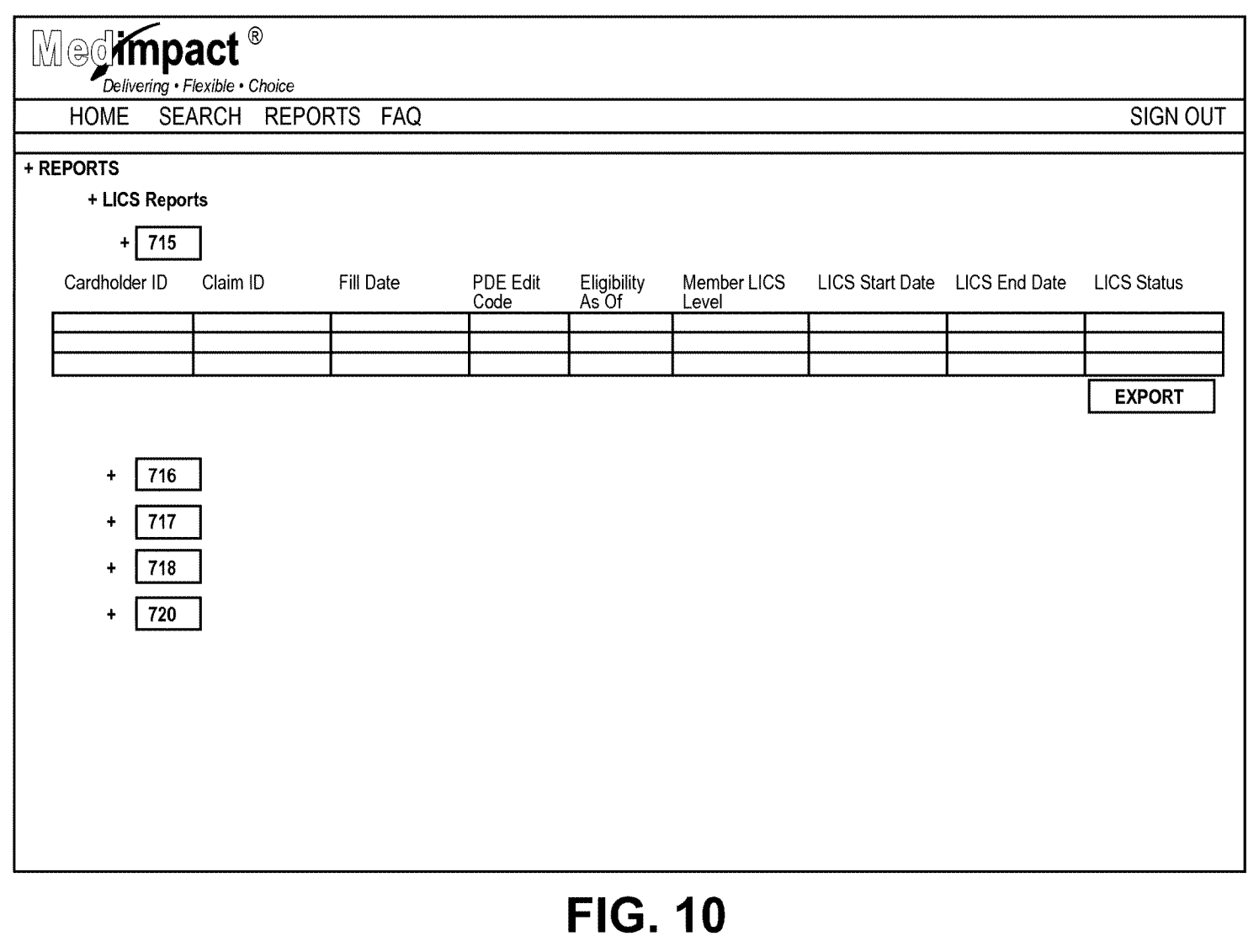

As mentioned above, many of the pages of the web-based interface include a toolbar 620 of hyperlinks, including a link to a reports page 623. The reports page offers access to a number of reports as described above with respect to FIG. 5. FIG. 10 and FIG. 11 are screenshots of examples of reports.

FIG. 10 is a screenshot of an example of an LICS Report. PDE edits codes 715-722 fall into the LICS edit category. The example LICS Report of FIG. 10 contains buttons for edit codes 715, 716, 717, 718, and 720. By clicking one of the buttons, a table is expanded or collapsed showing the records edited with the edit code associated with the button. This information can be exportable. In one embodiment, the information can be exported as a CSV file. In another embodiment, the information can be exported as a Microsoft Excel spreadsheet. In yet another embodiment, the information may be formatted and presented as a Portable Document Format (PDF) file. Although not explicitly described, it is to be appreciated that other information presented via the web interface, for example as described elsewhere herein, can be exportable in the manner described above. The LICS Report is particularly beneficial as LICS-related edits make up a large percentage of overall PDE edits.

FIG. 11 is a screenshot of an example of a PDE Summary Report. The PDE Summary Report of FIG. 11 displays a table illustrating the number of new PDE edits in the current cycle, the number of PDE edits in the current month, and the number of outstanding PDE edits year-to-date summarized by edit code groups. This information is also exportable, e.g., as a CSV file.

Another Example of a Web-Based Interface

FIGS. 12-22 illustrate another example of an embodiment of the web-based interface. As noted above, upon directing a suitable web browser to the Uniform Resource Locator (URL) of the web-based interface, the user is presented with a login screen, illustrated in FIG. 12. The login screen includes fields for entering a user ID 1210 and a password 1220. Upon entering a matching user ID and password and clicking a "SIGN IN" link 1230, the user is directed to a product selection screen.

Figure 13:
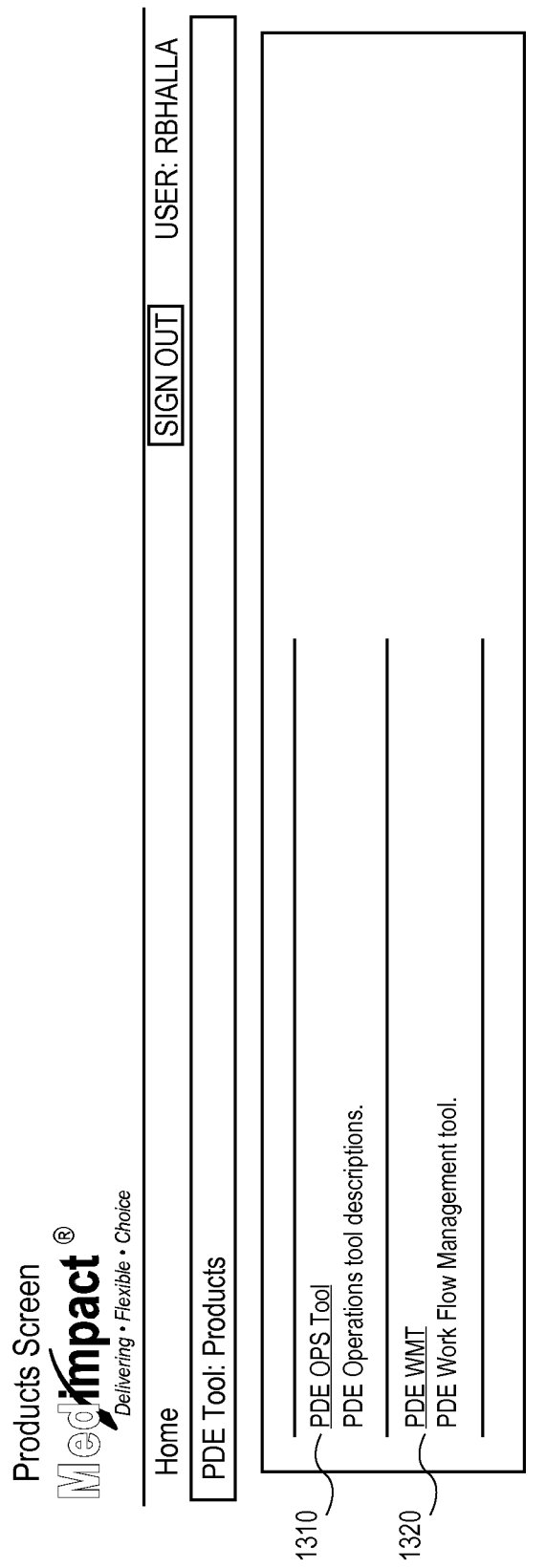
FIG. 13 is a screenshot of an example of a product selection screen.

FIG. 13 is a screenshot of an example of a product selection screen. The screen can provide links to any desired product. From the depicted screen, the user can select either a "PDE operations" tool 1310 which, among other things, allows a user to generate PDE files, or a "PDE workflow management" tool 1320 which, among other things, allows a user to track and correct errors. For example, the PDE operations tool can function as described above and elsewhere herein. For example, the PDE workflow management tool can function as described above and elsewhere herein.

Upon the user clicking the PDE workflow management tool link 1320, the user is directed to a dashboard screen. FIG. 14 is a screenshot of an example of a dashboard screen. The bulk of the screen is occupied by an interactive table 1410 detailing the number of records rejected per PDE edit code group for a given time period. The table 1410 of FIG. 14, for example, illustrates the number of records per PDE edit code group which were first rejected in the current cycle, which were resubmitted and rejected in the current cycle, and which are currently pending as rejected. This screen can provide information in a manner that the DDPS reports from CMS do not and provide. The screen can be very beneficial to the user by permitting the user to prioritize efforts in any of a variety of ways.

Upon the user clicking one of the entries in the table 1410, the user is directed to a report screen. FIG. 15 is a screenshot of an example of a report screen. Various information regarding the claims of the group selected from the table 1410 are presented in the report screen, including CMS Plan Code, Claim ID, Submission Status, PDE Edit Code, LICS Level, Current Cycle, Cycle First Rejected, Fill Date, etc.

Figure 16:
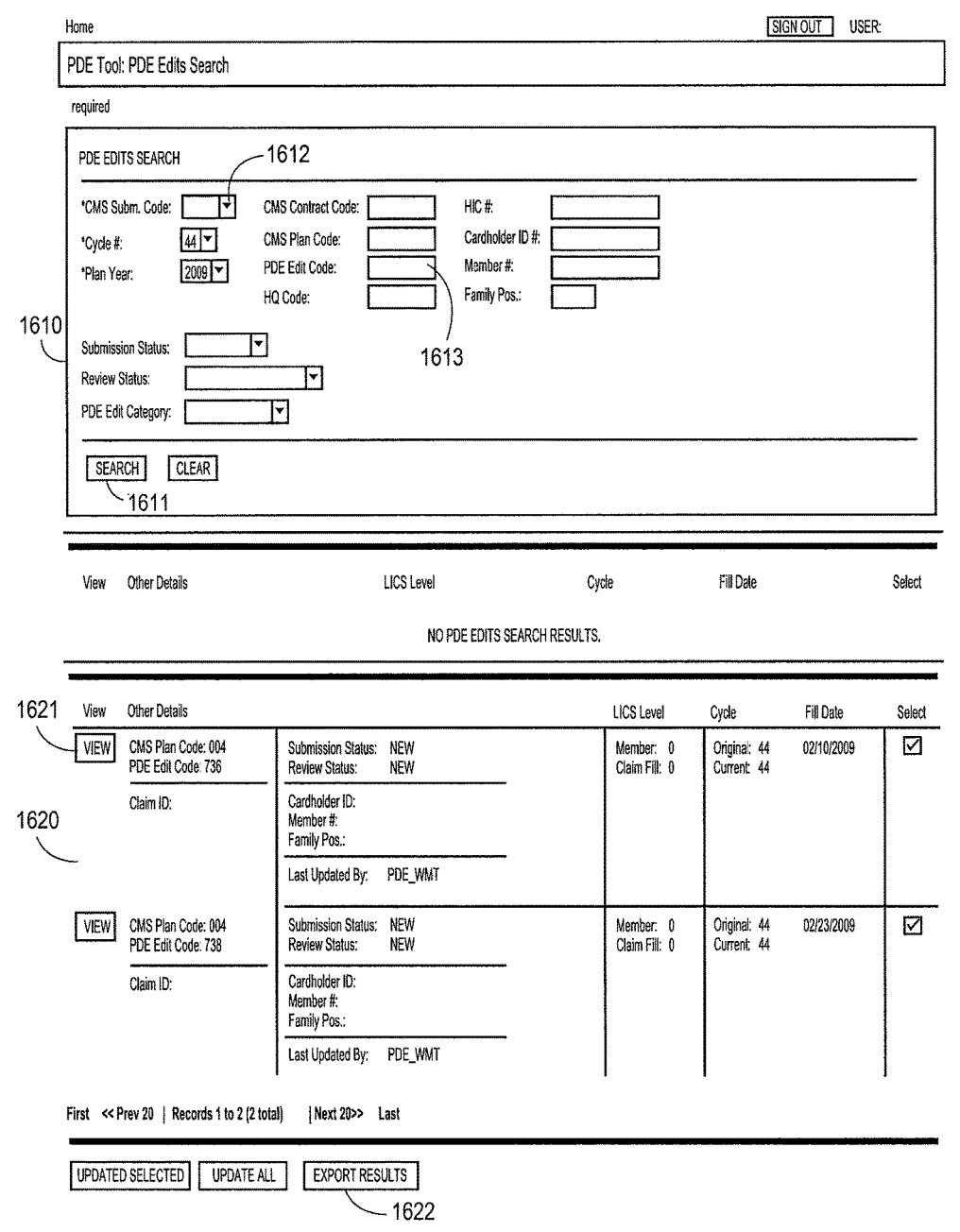

The screenshot of FIG. 14 also includes a link 1420 to a search page. FIG. 16 is a screenshot of an example of a search page screen. The search page includes a search area 1610 for the user to input search criteria and a results area 1620 for the user to view results of the search. Both the search area 1610 and the results area 1620 are collapsible and expandable to allow the user to more efficiently use the screen space.

As mentioned above with respect to FIG. 4, the search criteria can include a variety of different fields. In response to the user clicking the "SEARCH" button 1611, a query based on information input into these fields is submitted. In one embodiment, upon the user clicking certain of the input fields, a drop-down menu is presented showing the available search criteria. For example, upon the user clicking the CMS Submitter Code field 1612, the user may be presented with the CMS Submitter Codes previously associated with the user. Such information may be provided as part of the registration information described above with respect to block 410 of FIG. 4. As another example, upon clicking the PDE Edit Code field 1613, the user is presented with a drop-down menu listing the currently used edit codes. The drop-down menu may be sorted based on predefined priority rules or recent search history. The drop-down menu can also indicate the meaning of the available PDE edit codes. In another embodiment, the search page also include a PDE Edit Code Group field, which upon being clicked, presents the user with a list of PDE edit code groups, such as those described above with respect to FIG. 6 or shown in FIG. 14. Upon selection of one of these groups, the user can further narrow the search by selecting a PDE edit code from the group in a drop-down menu of the PDE Edit Code field 1613.

In response to the user clicking the "SEARCH" button 1611, the system executes a search and provides the search results, which are displayed in the results area 1620. The results area 1620 displays information about the claim records matching the criteria of the search.

The search area 1620 also includes an "EXPORT" button 1622, which, when clicked by a user, prompts the system to generate and submit the results in a downloadable file format, such as CSV. Other results of the system are exportable as well, as shown by the "EXPORT" button present in previous Figures.

In response to the user clicking on one of the results or one of the "VIEW" buttons 1621 proximal to each result, the user is directed to a record page with additional information regarding the specific claim record. FIG. 17 is a screenshot of an example of a record page. The record page includes a data area 1710 and a history area 1630. The data area 1710 displays information regarding a specific claim record. In one embodiment, the data area 1710 can be revised by the user. The revision may be automatically recorded and displayed in a history area 1730 or noted by the addition of a comment by the user into the history area 1730. The history area 1730 can be added to by the system to by the user in the form of comments. The history area 1730 includes a link 1733 to an add comments page, such as that shown in FIG. 18. Comments can include statements assigning responsibility to resolve the edits to certain persons or the strategy to be used in resolving the edit. The history area 1730 also displays comments previously entered. In one embodiment, the user is presented with a "quick comment" option which presents a list of text strings for selection either pre-defined by the system or the user.

The screenshot of FIG. 14 also includes a link 1425 to an import file selection page. As discussed with respect to FIG. 3, previously generated PDE files and errors may be loaded or imported into the claim management system 200 of FIG. 2. FIG. 19 is a screenshot of an import file selection page for selecting such a file. A user may click the browse link 1910 to find a file for selection. FIG. 20 is a screenshot of an example of such an import file. After selecting the file, a user can select the upload link 1920 to upload the file to the system.

The screenshot of FIG. 14 also includes a link 1430 to an import file search page. Selecting the link 1430 allows the user to find and review previously imported files. FIG. 21 is a screenshot of an example of an import file search page. The search page includes various fields in the area 2110, with parameters for a file search. For example, the area 2110 includes fields for a file name, file status, the identity of the user that imported the file, the date of import, and the plan year of the imported data. A user may enter search criteria in one or more of the fields and select a search link 2120 to search for imported files that match the entered search criteria. The results of the search may further be displayed in a display area 2130. The display area 2130 displays the details of imported files that match the search criteria. A user may click on a view link 2135 associated with each imported file that matches the search criteria to review a particular imported file. The details of the particular imported file may be shown in a claim import detail page. FIG. 22 is a screenshot of an example of a claim import detail page.

FIGS. 23-36 illustrate example screenshots of a web-interface that provides the user an interface for controlling the claim management system 200 to create PDE files and track errors as described above. For example, FIG. 23 illustrates a homepage from various options of services/processes the claim management system 200 can perform. FIGS. 24-36 illustrate screenshots of pages that can be accessed directly or indirectly via the homepage of FIG. 23. It should be noted that any suitable interface may be used to implement the functionality described above.

As mentioned above, embodiments of the web interface allow a user to "drill down" to view information more specifically. For example, the table 1410 in FIG. 14 provides clickable links to a report screen shown in FIG. 15 in which the presented records are filtered by the row and column of the entry of the table clicked. Further, each entry of the report screen is provided a clickable link to a record view screen shown in FIG. 17 in which the selected record is shown in detail, including a cumulative history of the record, such as changes made to the record or comments added to the record. Thus, the systems and methods may provide benefits that are not present absent the system or methods.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more example embodiments, the functions described may be implemented in hardware, software, or firmware executed on a processor, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

What is claimed is:

1. A method of generating and updating a formatted Prescription Drug Event file on a server, the method comprising:

providing a computer program with a web-based interface to a service provider computer system, the service provider computer system containing a covered amount and a non-covered amount for a prescription for a patient;

receiving claim information comprising a claim identifier, a patient identifier for the patient, and a prescription drug identifier for the prescription from a user via the web-based interface;

storing the claim identifier, the patient identifier, and the prescription drug identifier in a server memory;

receiving eligibility information comprising an identifier identifying a patient as a Medicare beneficiary from the user via the web-based interface;

storing the eligibility information in the server memory;

determining financial information based at least in part on a portion of the received claim information and a portion of the eligibility information;

generating a Prescription Drug Event (PDE) file for adjudication based at least in part on the portion of the claim information, the portion of the eligibility information, and the financial information;

electronically transmitting the PDE file to a Centers for Medicare and Medicaid Services (CMS) computer;

receiving updated claim or eligibility information from the user via the web-based interface, the updated claim or eligibility information pertaining to the PDE file;

storing the updated claim or eligibility information electronically;

electronically receiving a rejection of the PDE file from the CMS computer;

detecting potential errors by calculating additional fields in the PDE file based upon error trends and root cause analysis for previously tracked errors, the claim information and the eligibility information and the updated claim or eligibility information;

checking the additional fields for financial and format errors;

automatically loading and updating the rejected PDE file to include the updated claim or eligibility information;

automatically submitting the updated rejected PDE file to the CMS computer based at least on the checking the additional fields for financial and format errors;

receiving, subsequent to automatically submitting the updated rejected PDE file to the CMS computer, one of a rejection of the updated rejected PDE file and an acceptance of the updated rejected PDE file from the CMS computer;

consequent to receiving the rejection of the updated rejected PDE file from the CMS computer:

associating an edit code with the claim associated with the PDE file; and transmitting the edit code and the updated rejected PDE file to the service provider computer system, wherein a report is generated by the program on the service provider computer system comprising the edit code and claim identifier; and consequent to receiving the acceptance of the updated rejected PDE file from the CMS computer:

transmitting reimbursement and eligibility information to the service provider computer system, wherein the covered amount and non-covered amount for the prescription is updated and the eligibility status for the patient is updated to eligible by the program on the service provider computer system.

2. The method of claim 1, further comprising transmitting the PDE file to the user via the web-based interface.

3. The method of claim 1, wherein the claim information is indicative of a plurality of pharmaceutical transactions.

4. The method of claim 1, further comprising:

validating the determined financial information.

5. A system for generating and updating a formatted Prescription Drug Event file, the system comprising:

a transmitter configured to transmit a computer program with a web-based interface to a service provider computer system, the service provider computer system containing a covered amount and a non-covered amount for a prescription;

a receiver configured to receive claim information and eligibility information from a user via a web-based interface;

a processor configured to determine financial information based at least in part on a portion of the received claim information and a portion of the eligibility information, wherein the processor is further configured to generate a Prescription Drug Event (PDE) file for adjudication based at least in part on the portion of the claim information, the portion of the eligibility information, and the financial information;

the transmitter further configured to electronically transmit the PDE file to a Centers for Medicare and Medicaid Services (CMS) computer; and a system memory configured to store the claim information, the eligibility information, and the financial information;

wherein, the receiver is further configured to:

receive updated claim or eligibility information from the user via the web-based interface, the updated claim or eligibility information pertaining to the PDE file, and electronically receive a rejection of the PDE file from the CMS computer;

wherein the processor is further configured to:

store the updated claim or eligibility information electronically;

detect potential errors by calculating additional fields in the PDE file based upon error trends and root cause analysis for previously tracked errors, the claim information and the eligibility information and the updated claim or eligibility information;

check the additional fields for financial and format errors; and automatically load and update the rejected PDE file to include the updated claim or eligibility information; and wherein the transmitter is further configured to automatically submit the updated rejected PDE file to the CMS computer based at least on the check the additional fields for financial and format errors; and wherein the transmitter, subsequent to receiving a rejection of the updated rejected PDE file from the CMS computer by the receiver, is further configured to:

associate an edit code with the claim associated with the PDE file; and transmit the updated rejected PDE file and an associated edit code to the service provider computer system, wherein the computer program on the service provider computer system generates a report comprising the edit code and claim identifier.

6. The system of claim 5, wherein the memory comprises a web-accessible database.

7. The system of claim 5, wherein the transmitter is further configured to transmit the PDE file to the user via the web-based interface.

8. The system of claim 5, wherein the processor is further configured to validate the determined financial information.

9. A method of updating medical claims implemented by a claims management system comprising a processor and memory, the method comprising:
- providing a computer program with a web-based interface to a service provider computer system, the service provider computer system containing a covered amount and a non-covered amount for a prescription;
- storing a plurality of claim files in an electronic database in system memory, each claim file associated with a unique claim number and comprising claim information and eligibility information;
- electronically receiving updated claim or eligibility information from a user of the computer program, the updated claim or eligibility information pertaining to one or more of the plurality of claim files in the database;
- storing the updated claim or eligibility information in the electronic database in the system memory
- electronically receiving rejected claim files from a payor, wherein the rejected claim files correspond to at least a portion of the plurality of claim files stored in the electronic database;
- automatically loading the rejected claim files and automatically updating at least a portion of the rejected claim files upon loading to include at least a portion of the updated claim or eligibility information;
- detecting potential errors by calculating additional fields in the at least a portion of the plurality of claim files, the calculation based upon error trends and root cause analysis for previously tracked errors, the claim information and the eligibility information and the updated claim or eligibility information;
- checking the additional fields for financial and format errors; and
- automatically submitting the updated rejected claim files to the payor based at least on the checking the additional fields for financial and format errors;
- consequent to the updated rejected claim files subsequently accepted by the payor:
  - transmitting reimbursement and eligibility information to the service provider computer system;
  - updating the covered amount and non-covered amount for the prescription by the program on the service provider computer system; and
  - updating an eligibility status for the patient to eligible.

10. The method of claim 9, wherein the updated claim or eligibility information is received from the user via a web-based interface.

11. The method of claim 9, wherein each of the plurality of claim files is a PDE file.

12. The method of claim 9, wherein the payor is the Centers for Medicare and Medicaid Services (CMS).

* * * * *